United States Patent
Zhang et al.

(10) Patent No.: US 12,295,736 B2
(45) Date of Patent: *May 13, 2025

(54) MEDICAL DEVICE AND METHOD FOR DETECTING ELECTRICAL SIGNAL NOISE

(71) Applicant: Medtronic, Inc., Minneapolis, MN (US)

(72) Inventors: Xusheng Zhang, Shoreview, MN (US); Saul E. Greenhut, Denver, CO (US); Yuanzhen Liu, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 113 days.

This patent is subject to a terminal disclaimer.

(21) Appl. No.: 18/193,457

(22) Filed: Mar. 30, 2023

(65) Prior Publication Data

US 2023/0233131 A1    Jul. 27, 2023

Related U.S. Application Data

(63) Continuation of application No. 17/172,770, filed on Feb. 10, 2021, now Pat. No. 11,617,534.

(60) Provisional application No. 62/976,822, filed on Feb. 14, 2020.

(51) Int. Cl.
| | | |
|---|---|---|
| *A61B 5/00* | (2006.01) | |
| *A61B 5/29* | (2021.01) | |
| *A61B 5/363* | (2021.01) | |

(52) U.S. Cl.
CPC .............. *A61B 5/363* (2021.01); *A61B 5/29* (2021.01); *A61B 5/4836* (2013.01); *A61B 5/686* (2013.01); *A61B 5/7203* (2013.01); *A61B 5/7225* (2013.01); *A61B 5/7264* (2013.01)

(58) Field of Classification Search
CPC ...................... A61B 5/363; A61B 5/29; A61B 5/7203–7217; A61B 5/4836; A61B 5/686; A61B 5/7225; A61B 5/7264

See application file for complete search history.

(56) References Cited

U.S. PATENT DOCUMENTS

| | | |
|---|---|---|
| 4,381,786 A | 5/1983 | Duggan |
| 4,880,004 A | 11/1989 | Baker et al. |
| 5,103,819 A | 4/1992 | Baker et al. |
| 6,321,115 B1 | 11/2001 | Mouchawar et al. |
| 6,434,426 B1 | 8/2002 | Munneke et al. |
| 8,175,708 B1 | 5/2012 | Snell et al. |
| 8,744,556 B2 | 6/2014 | Mahajan et al. |

(Continued)

OTHER PUBLICATIONS

"Office Action Issued in European Patent Application No. 24165868. 1", Mailed Date: May 29, 2024, 8 Pages.

(Continued)

*Primary Examiner* — Scott M. Getzow

(57) ABSTRACT

A medical device is configured to sense an electrical signal and determine that signal to noise criteria are met based on electrical signal segments stored in response to sensed electrophysiological events. The medical device is configured to determine an increased gain signal segment from one of the stored electrical signal segments in response to determining that the signal to noise criteria are met. The medical device determines a noise metric from the increased gain signal segment. The stored electrical signal segment associated with the increased gain signal segment may be classified as a noise segment in response to the noise metric meeting noise detection criteria.

21 Claims, 15 Drawing Sheets

(56) References Cited

U.S. PATENT DOCUMENTS

| | | |
|---|---|---|
| 8,825,145 B1 | 9/2014 | Zhang |
| 9,174,062 B2 | 11/2015 | Stadler et al. |
| 9,566,012 B2 | 2/2017 | Greenhut et al. |
| 10,226,639 B2 | 3/2019 | Zhang |
| 10,252,071 B2 | 4/2019 | Cao et al. |
| 10,406,373 B2 | 9/2019 | Zhang |
| 10,470,681 B2 | 11/2019 | Greenhut et al. |
| 2010/0312131 A1 | 12/2010 | Naware et al. |
| 2012/0108990 A1 | 5/2012 | Stadler et al. |
| 2016/0158567 A1 | 6/2016 | Marshall et al. |
| 2018/0028083 A1 | 2/2018 | Greenhut et al. |
| 2018/0028085 A1 | 2/2018 | Zhang et al. |
| 2018/0028828 A1 | 2/2018 | Cao et al. |
| 2018/0207436 A1 | 7/2018 | Zhang |
| 2018/0207437 A1 | 7/2018 | Zhang et al. |

OTHER PUBLICATIONS

PCT Search Report and PCT Written Opinion of the International Searching Authority mailed on Jun. 7, 2021, corresponding to counterpart A0002598WO01, PCT Application No. PCT/US2021/017750, 12 pages.

MEDICAL DEVICE AND METHOD FOR DETECTING ELECTRICAL SIGNAL NOISE

CROSS-REFERENCE TO RELATED APPLICATIONS

This application is a Continuation of U.S. patent application Ser. No. 17/172,770 (published as U.S. Patent Application Publication No. 2021/0251551), filed on Feb. 10, 2021, which claims the benefit of and priority to U.S. Provisional Patent Application Ser. No. 62/976,822 filed Feb. 14, 2020, the entire content of both of which incorporated herein by reference.

TECHNICAL FIELD

The disclosure relates generally to a medical device and method for detecting electrical signal noise.

BACKGROUND

Medical devices may sense electrophysiological signals from the heart, brain, nerve, muscle or other tissue. Such devices may be implantable, wearable or external devices using implantable and/or surface (skin) electrodes for sensing the electrophysiological signals. In some cases, such devices may be configured to deliver a therapy based on the sensed electrophysiological signals. For example, implantable or external cardiac pacemakers, cardioverter defibrillators, cardiac monitors and the like, sense cardiac electrical signals from a patient's heart. A cardiac pacemaker or cardioverter defibrillator may deliver therapeutic electrical stimulation to the heart via electrodes carried by one or more medical electrical leads and/or electrodes on a housing of the medical device. The electrical stimulation may include signals such as pacing pulses or cardioversion or defibrillation shocks. In some cases, a medical device may sense cardiac electrical signals attendant to the intrinsic or pacing-evoked depolarizations of the heart and control delivery of stimulation signals to the heart based on sensed cardiac electrical signals. Upon detection of an abnormal rhythm, such as bradycardia, tachycardia or fibrillation, an appropriate electrical stimulation signal or signals may be delivered to restore or maintain a more normal rhythm of the heart. For example, an implantable cardioverter defibrillator (ICD) may deliver pacing pulses to the heart of the patient upon detecting bradycardia or tachycardia or deliver cardioversion or defibrillation (CV/DF) shocks to the heart upon detecting tachycardia or fibrillation.

A medical device may sense cardiac electrical signals from a heart chamber and deliver electrical stimulation therapies to the heart chamber using electrodes carried by a transvenous medical electrical lead. Cardiac signals sensed within a heart chamber using endocardial electrodes, for example, generally have a high signal strength and quality for reliably sensing near-field cardiac electrical events, such as ventricular R-waves sensed from within a ventricle. In some proposed or available ICD systems, an extra-cardiac lead may be coupled to the ICD, in which case cardiac signal sensing from outside the heart presents challenges in accurately sensing cardiac electrical events. In various medical devices or medical device systems, implantable, transcutaneous, or cutaneous (skin) electrodes may be positioned for sensing an electrophysiological signal by the medical device, which may be an implantable, external or wearable medical device. Such devices may include devices configured to monitor an electrophysiological signal for a medical condition or health purposes (including, but not limited to fitness trackers, watches, or other medical or fitness devices).

SUMMARY

In general, the disclosure is directed to a medical device and techniques for detecting noise in an electrical signal sensed by the medical device. The electrical signal noise may be detected in an electrophysiological signal such as, but not limited to, a cardiac electrical signal, nerve signal, brain signal, or muscle signal. The noise detection techniques may be used in conjunction with a variety of patient monitoring devices and/or therapy delivery devices, including devices that monitor a patient heart rate. For example, detection of noise in a cardiac electrical signal may be included in heart rate monitoring and arrhythmia detection methods, such as a tachyarrhythmia detection algorithm, to avoid false arrhythmia detection in the presence of cardiac electrical signal noise, such as electromagnetic interference (EMI) or non-cardiac myopotential signals. A device operating according to the techniques disclosed herein may determine if signal to noise criteria are met based on an electrical signal sensed by the device and increase the gain of an electrical signal segment in response to determining that the signal to noise criteria are met. The device may determine a noise metric from the increased gain signal segment. An electrical signal segment associated with the increased gain signal segment may be classified as noise based on the noise metric. The noise detection techniques disclosed herein may improve electrophysiological signal monitoring by rejecting or ignoring noise segments and may avoid delivery of unnecessary therapy (or withholding of a necessary therapy) in medical devices that include therapy delivery capabilities.

In some examples, a medical device as disclosed herein may be configured to detect ventricular tachyarrhythmia, e.g., ventricular tachycardia (VT) or ventricular fibrillation (VF), based on detecting a ventricular rate that is faster than a tachyarrhythmia detection rate for at least a predetermined number of ventricular cycles. The VT or VF rate may be detected by sensing R-waves from a cardiac electrical signal, determining ventricular intervals or RR intervals (RRIs) between consecutively sensed R-waves, and counting the number of ventricular intervals that are shorter than VT or VF detection intervals. Non-cardiac noise may be oversensed as ventricular R-waves due to cardiac signal amplitude variability and/or due to episodes of non-cardiac noise, such as skeletal muscle myopotentials, e.g., during patient activity. Oversensing of non-cardiac noise may cause the medical device to falsely increase the count of VT or VF intervals when an underlying normal sinus rhythm may be present. A medical device operating according to the techniques disclosed herein may detect noise in cardiac electrical signal segments, which may be occurring during a series of ventricular intervals that include tachyarrhythmia detection intervals. The device is configured to improve detection of non-cardiac noise by determining when signal to noise criteria are met and increase the gain of a cardiac signal segment being evaluated for noise detection to reveal low amplitude non-cardiac noise pulses that may be present. When noise is detected in the cardiac electrical signal and an arrhythmia detection criterion is satisfied, such as a threshold number of tachyarrhythmia intervals, the arrhythmia detection may be withheld to avoid false arrhythmia detection and avoid delivery of unnecessary therapy.

In one example, the disclosure provides a medical device including a sensing circuit, a memory, and a control circuit. The sensing circuit is configured to sense at least one electrical signal and sense electrophysiological events from the at least one electrical signal. The control circuit is coupled to the sensing circuit and the memory and is configured to store an electrical signal segment from the at least one electrical signal sensed by the sensing circuit in the memory in response to each one of a series of electrophysiological events sensed by the sensing circuit. The control circuit is configured to determine that signal to noise criteria are met based on the stored electrical signal segments and determine an increased gain signal segment from one of the cardiac electrical signal segments in response to determining that the signal to noise criteria are met. The control circuit is configured to determine a noise metric from the increased gain signal segment, determine that the noise metric meets noise detection criteria, and classify the stored electrical signal segment associated with the increased gain signal segment as a noise segment in response to the noise metric meeting the noise detection criteria. The control circuit may determine that a tachyarrhythmia detection criterion is met for detecting a tachyarrhythmia based on the at least one electrical signal and withhold a tachyarrhythmia detection in response to the stored electrical signal segment being classified as a noise segment.

In another example, the disclosure provides a method that includes sensing at least one electrical signal, sensing electrophysiological events from the at least one electrical signal, storing an electrical signal segment from the at least one electrical signal in response to each one of a series of sensed electrophysiological events. The method further includes determining that signal to noise criteria are met based on the stored electrical signal segments, determining an increased gain signal segment from one of the stored cardiac electrical signal segments in response to determining that the signal to noise criteria are met, and determining a noise metric from the increased gain signal segment. The method includes determining that the noise metric meets a noise detection criteria and classifying the stored cardiac electrical signal segment associated with the increased gain signal segment as a noise segment in response to the noise metric meeting the noise detection criteria. The method may include determining that a tachyarrhythmia detection criterion is met for detecting a tachyarrhythmia based on the at least one electrical signal and withholding a tachyarrhythmia detection in response to the stored electrical signal segment being classified as a noise segment.

In another example, the disclosure provides a non-transitory computer-readable medium storing a set of instructions which, when executed by a control circuit of a medical device, cause the medical device to sense at least one electrical signal, sense electrophysiological events from the at least one electrical signal, and store an electrical signal segment from the at least one electrical signal in response to each one of a series of sensed electrophysiological events. The instructions further cause the medical device to determine that signal to noise criteria are met based on the stored electrical signal segments, determine an increased gain signal segment from one of the stored electrical signal segments in response to determining that the signal to noise criteria are met, determine a noise metric from the increased gain signal segment and classify the stored electrical signal segment associated with the increased gain signal segment as a noise segment in response to the noise metric meeting noise detection criteria. The instructions may further cause the medical device to determine that a tachyarrhythmia detection criterion is met for detecting a tachyarrhythmia based on the at least one electrical signal and withhold a tachyarrhythmia detection in response to the stored electrical signal segment being classified as a noise segment.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

Figure 1A:
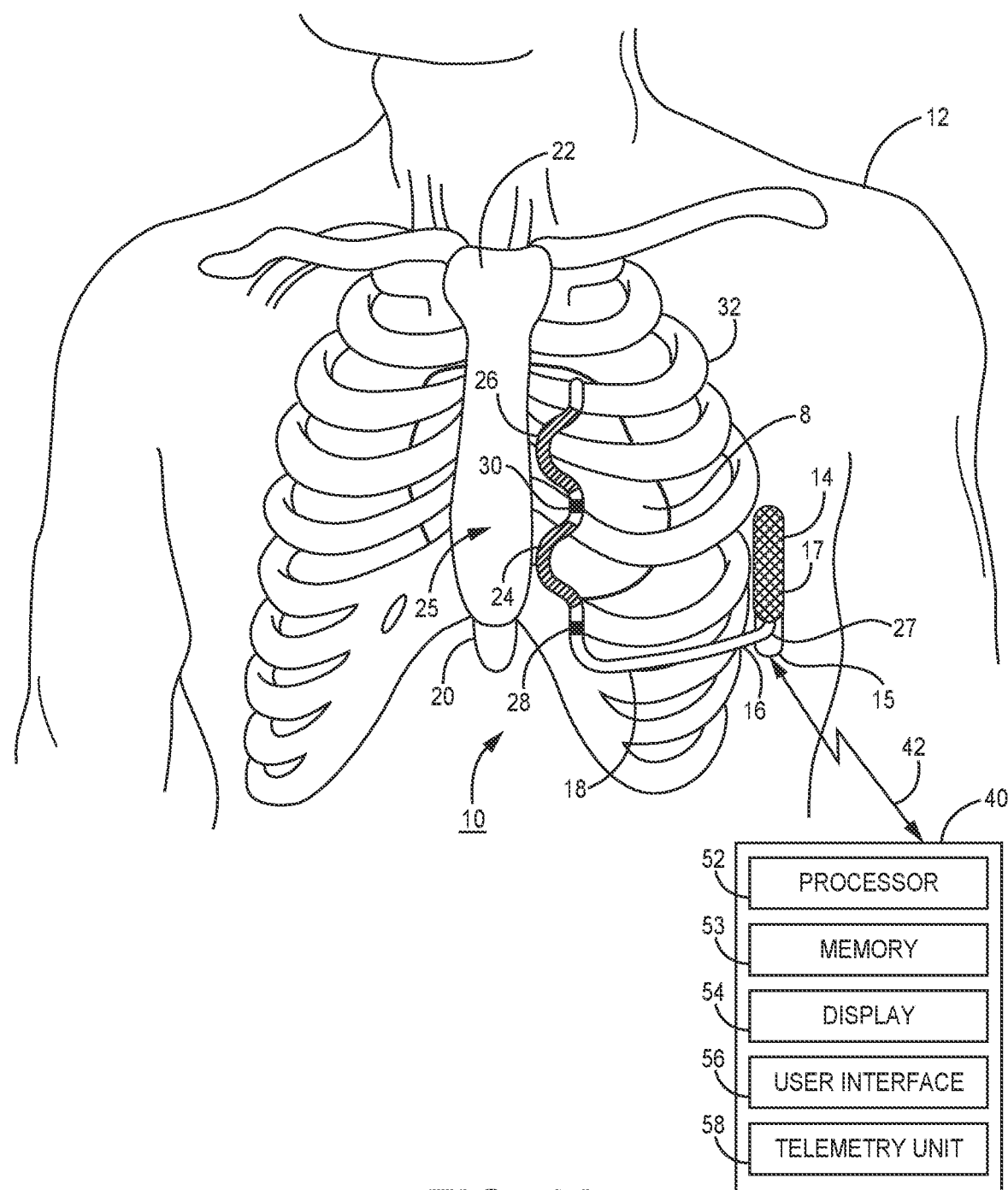
FIGS. 1A and 1B are conceptual diagrams of an extra-cardiovascular ICD system configured to sense cardiac electrical events and deliver cardiac electrical stimulation therapies according to one example.

In general, this disclosure describes a medical device and techniques for detecting noise in an electrical signal sensed by the medical device, such as a cardiac electrical signal. In some examples, the medical device may be configured to sense cardiac electrical events, e.g., atrial P-waves attendant to atrial myocardial depolarizations and/or ventricular R-waves attendant to ventricular myocardial depolarizations from the cardiac electrical signal. The medical device may determine the heart rate or rhythm and a need for therapy delivery based on at least the sensed cardiac electrical events. For example, atrial or ventricular tachyarrhythmia may be detected by the medical device based on sensed cardiac electrical signals. In some examples, the medical device may be configured to sense R-waves attendant to ventricular depolarizations from a cardiac electrical signal for use in controlling ventricular pacing and detecting ventricular tachyarrhythmias. A ventricular tachyarrhythmia may be detected in response to sensing a threshold number of R-waves occurring at a time interval from a preceding R-wave that is less than a tachyarrhythmia detection interval. Non-cardiac electrical noise present in the cardiac signal, e.g., electromagnetic interference (EMI) or skeletal muscle myopotential signals, may be oversensed as R-waves, resulting in false, short RRIs being determined as ventricular tachyarrhythmia intervals. In some instances, variability in the R-wave signal strength due to patient motion or other factors may result in oversensing of non-cardiac noise, leading to relatively short RRIs being counted toward tachyarrhythmia detection when the underlying rhythm may actually be a normal sinus rhythm. False tachyarrhythmia detection may lead to a CV/DF shock or other tachyarrhythmia therapy delivered by the medical device, such as anti-tachyarrhythmia pacing (ATP), when a therapy may not be needed.

In some examples, the medical device performing the techniques disclosed herein may be included in an extra-cardiovascular ICD system. As used herein, the term "extra-cardiovascular" refers to a position outside the blood vessels, heart, and pericardium surrounding the heart of a patient. Implantable electrodes carried by extra-cardiovascular leads may be positioned extra-thoracically (outside the ribcage and sternum) or intra-thoracically (beneath the ribcage or sternum) but generally not in intimate contact with myocardial tissue. In other examples, transvenous extra-cardiac leads may carry implantable electrodes that can be positioned intravenously but outside the heart, e.g., within the internal thoracic vein, jugular vein, or other vein, for sensing cardiac electrical signals. Patient positional changes or patient physical activity as well as other factors may lead to variation in the cardiac event signal amplitudes, e.g., P-wave amplitudes, R-wave amplitudes and T-wave amplitudes, in the signal sensed from an extra-cardiovascular or extra-cardiac location. Furthermore, the presence and amplitude of skeletal muscle myopotential signals in a cardiac electrical signal may be highly variable due to varying physical activity and posture of the patient. Cardiac signals sensed via extra-cardiovascular or extra-cardiac electrodes may be more susceptible to signal amplitude variability and noise contamination, e.g., due to myopotentials or environmental EMI, than cardiac signals sensed using transvenous intracardiac electrodes.

The medical device and techniques disclosed herein provide a method for detecting noise, such as myopotential noise, by increasing the gain of a cardiac electrical signal being analyzed for noise to avoid underdetection of the signal noise by a noise detection algorithm. By increasing the gain of the cardiac electrical signal, non-cardiac noise may be more reliably detected, enabling false tachyarrhythmia detection due to non-cardiac noise oversensing to be rejected. As disclosed herein, the medical device may detect noise from a cardiac electrical signal based on one or more noise metrics determined from a cardiac electrical signal segment. When the amplitude of noise pulses in the cardiac electrical signal is low, e.g., less than a threshold, the gain of the cardiac electrical signal is increased to intentionally increase the amplitude of the noise pulses to improve the likelihood of detecting non-cardiac noise present in the cardiac electrical signal that may be leading to false cardiac event sensing.

Noise detection techniques are described herein in conjunction with an ICD configured to sense cardiac electrical signals using an implantable extra-cardiovascular (or extra-cardiac) medical lead carrying sensing and therapy delivery electrodes. Aspects disclosed herein, however, may be utilized in conjunction with other cardiac medical devices or systems and more generally with other medical devices or systems configured to sense electrical signals in which the electrical signal can become noise corrupted. For example, the noise detection techniques as described in conjunction with the accompanying drawings may be implemented in any implantable or external medical device enabled for sensing electrophysiological signals including brain, nerve, and muscle signals. The noise detection techniques may be used in conjunction with medical devices configured to sense cardiac electrical events from cardiac signals received from a patient's heart via sensing electrodes, including implantable pacemakers, ICDs or cardiac monitors coupled to non-transvenous, transvenous, pericardial, or epicardial sensing electrodes; leadless pacemakers, ICDs, cardiac monitors having housing-based sensing electrodes; and external or wearable pacemakers, defibrillators, or cardiac monitors coupled to external, surface or skin electrodes. The noise detection apparatus and techniques disclosed herein may be implemented in a variety of medical devices that use implantable or external electrodes for sensing electrophysiological signals that may be noise corrupted.

The illustrative examples presented herein involve sensing cardiac electrical signals for the detection of ventricular tachyarrhythmia. The disclosed techniques, however, may be implemented in a medical device configured to sense atrial and/or ventricular cardiac events for detecting a variety of cardiac rhythms, such as bradycardia, tachycardia, fibrillation, etc. For example, a cardiac device using the disclosed noise detection techniques may be configured to sense P-waves, e.g., for detecting (and optionally treating) atrial tachyarrhythmia. In this case, the medical device may count PP intervals occurring between consecutively sensed atrial P-waves which are less than an atrial tachyarrhythmia detection interval. Cardiac electrical signals, which may be sensed from within or outside an atrial chamber, may be analyzed for detecting non-cardiac noise based on an analysis of the cardiac electrical signal using the techniques disclosed herein. An atrial tachyarrhythmia episode may be rejected based on non-cardiac noise detection.

More generally, the disclosed techniques may be used in any device that is configured to determine a heart rate from sensed cardiac electrical signals, such as fitness trackers, watches, or other heart rate monitors. When the cardiac electrical signal is corrupted by non-cardiac noise, the determined heart rate may be incorrect, e.g., overestimated, due to the non-cardiac noise signals being falsely sensed as cardiac events.

Figure 1B:
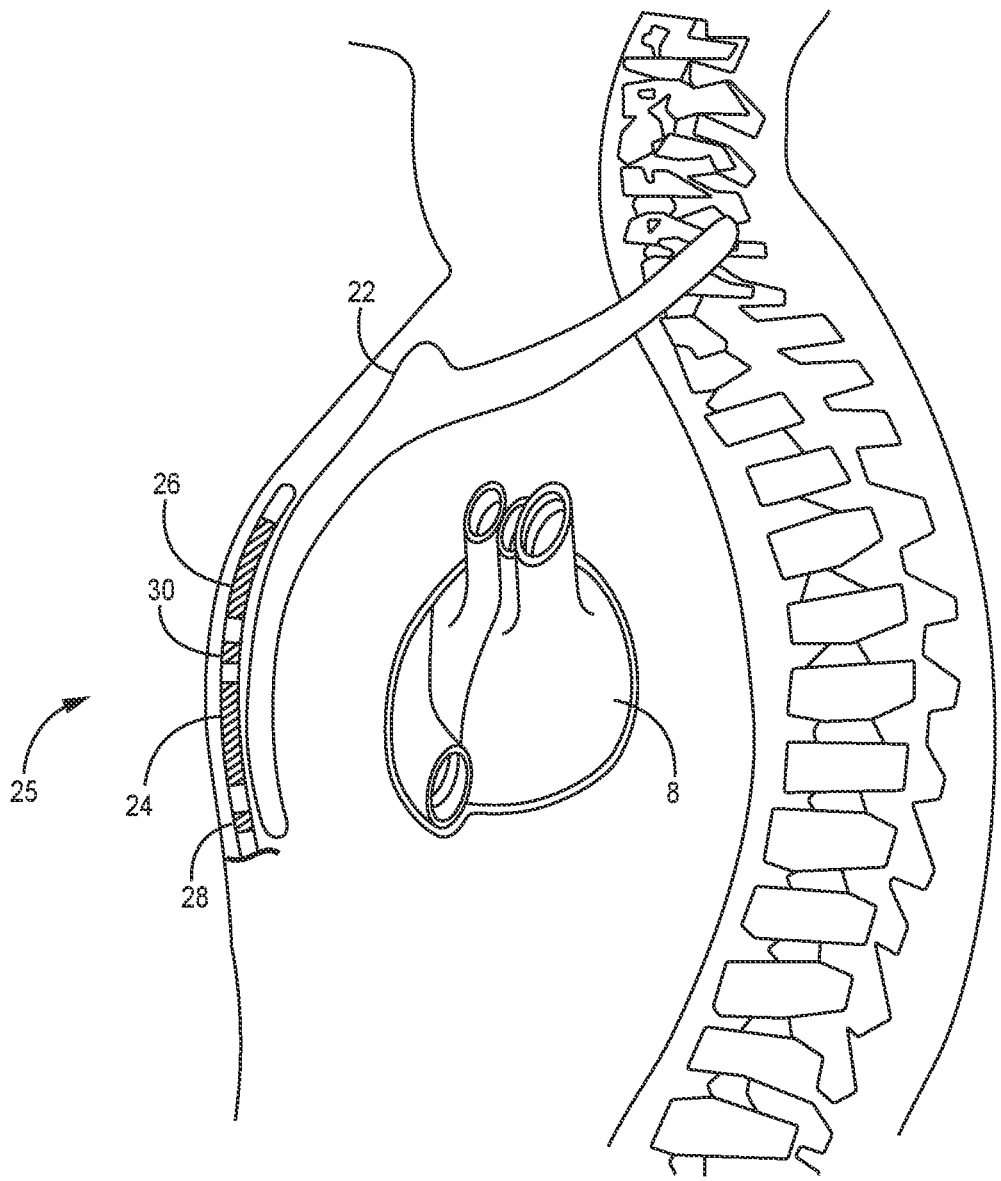

FIGS. 1A and 1B are conceptual diagrams of an extra-cardiovascular ICD system 10 configured to sense cardiac electrical events and deliver cardiac electrical stimulation therapies according to one example. FIG. 1A is a front view of ICD system 10 implanted within patient 12. FIG. 1B is a side view of ICD system 10 implanted within patient 12.

ICD system 10 includes an ICD 14 connected to an extra-cardiovascular electrical stimulation and sensing lead 16. FIGS. 1A and 1B are described in the context of an ICD system 10 capable of providing high voltage CV/DF shocks, and in some examples cardiac pacing pulses, in response to detecting a cardiac tachyarrhythmia. However, the techniques disclosed herein for detecting non-cardiac noise may be implemented in other cardiac devices configured for sensing cardiac events and, for example, determining a cardiac event interval or rate, for use in determining the cardiac rate or rhythm and controlling a cardiac electrical stimulation therapy.

ICD 14 includes a housing 15 that forms a hermetic seal that protects internal components of ICD 14. The housing 15 of ICD 14 may be formed of a conductive material, such as titanium or titanium alloy. The housing 15 may function as an electrode (sometimes referred to as a "can" electrode). Housing 15 may be used as an active can electrode for use in delivering CV/DF shocks or other high voltage pulses delivered using a high voltage therapy circuit. In other examples, housing 15 may be available for use in delivering unipolar, low voltage cardiac pacing pulses and/or for sensing cardiac electrical signals in combination with electrodes carried by lead 16. In other instances, the housing 15 of ICD 14 may include a plurality of electrodes on an outer portion of the housing. The outer portion(s) of the housing 15 functioning as an electrode(s) may be coated with a material, such as titanium nitride, e.g., for reducing post-stimulation polarization artifact.

ICD 14 includes a connector assembly 17 (also referred to as a connector block or header) that includes electrical feedthroughs crossing housing 15 to provide electrical connections between conductors extending within the lead body 18 of lead 16 and electronic components included within the housing 15 of ICD 14. As will be described in further detail herein, housing 15 may house one or more processors, memories, transceivers, cardiac electrical signal sensing circuitry, therapy delivery circuitry, power sources and other components for sensing cardiac electrical signals, detecting a heart rhythm, and controlling and delivering electrical stimulation pulses to treat an abnormal heart rhythm.

Elongated lead body 18 has a proximal end 27 that includes a lead connector (not shown) configured to be connected to ICD connector assembly 17 and a distal portion 25 that includes one or more electrodes. In the example illustrated in FIGS. 1A and 1B, the distal portion 25 of lead body 18 includes defibrillation electrodes 24 and 26 and pace/sense electrodes 28 and 30. In some cases, defibrillation electrodes 24 and 26 may together form a defibrillation electrode in that they may be configured to be activated concurrently. Alternatively, defibrillation electrodes 24 and 26 may form separate defibrillation electrodes in which case each of the electrodes 24 and 26 may be activated independently.

Electrodes 24 and 26 (and in some examples housing 15) are referred to herein as defibrillation electrodes because they are utilized, individually or collectively, for delivering high voltage stimulation therapy (e.g., cardioversion or defibrillation shocks). Electrodes 24 and 26 may be elongated coil electrodes and generally have a relatively high surface area for delivering high voltage electrical stimulation pulses compared to pacing and sensing electrodes 28 and 30. However, electrodes 24 and 26 and housing 15 may also be utilized to provide pacing functionality, sensing functionality or both pacing and sensing functionality in addition to or instead of high voltage stimulation therapy. In this sense, the use of the term "defibrillation electrode" herein should not be considered as limiting the electrodes 24 and 26 for use in only high voltage cardioversion/defibrillation shock therapy applications. For example, either of electrodes 24 and 26 may be used as a sensing electrode in a sensing vector for sensing cardiac electrical signals and determining a need for an electrical stimulation therapy.

Electrodes 28 and 30 are relatively smaller surface area electrodes which are available for use in sensing electrode vectors for sensing cardiac electrical signals and may be used for delivering relatively low voltage pacing pulses in some configurations. Electrodes 28 and 30 are referred to as pace/sense electrodes because they are generally configured for use in low voltage applications, e.g., used as either a cathode or anode for delivery of pacing pulses and/or sensing of cardiac electrical signals, as opposed to delivering high voltage CV/DF shocks. In some instances, electrodes 28 and 30 may provide only pacing functionality, only sensing functionality or both.

ICD 14 may obtain cardiac electrical signals corresponding to electrical activity of heart 8 via a combination of sensing electrode vectors that include combinations of electrodes 24, 26, 28 and/or 30. In some examples, housing 15 of ICD 14 is used in combination with one or more of electrodes 24, 26, 28 and/or 30 in a sensing electrode vector. Various sensing electrode vectors utilizing combinations of electrodes 24, 26, 28, and 30 and housing 15 are described below for sensing first and second cardiac electrical signals using respective first and second sensing electrode vectors that may be selected by sensing circuitry included in ICD 14.

In the example illustrated in FIGS. 1A and 1B, electrode 28 is located proximal to defibrillation electrode 24, and electrode 30 is located between defibrillation electrodes 24 and 26. One, two or more pace/sense electrodes may be carried by lead body 18. For instance, a third pace/sense electrode may be located distal to defibrillation electrode 26 in some examples. Electrodes 28 and 30 are illustrated as ring electrodes; however, electrodes 28 and 30 may comprise any of a number of different types of electrodes, including ring electrodes, short coil electrodes, hemispherical electrodes, directional electrodes, segmented electrodes, or the like. Electrodes 28 and 30 may be positioned at other locations along lead body 18 and are not limited to the positions shown. In other examples, lead 16 may include fewer or more pace/sense electrodes and/or defibrillation electrodes than the example shown here.

In the example shown, lead 16 extends subcutaneously or submuscularly over the ribcage 32 medially from the connector assembly 27 of ICD 14 toward a center of the torso of patient 12, e.g., toward xiphoid process 20 of patient 12. At a location near xiphoid process 20, lead 16 bends or turns and extends superiorly, subcutaneously or submuscularly, over the ribcage and/or sternum, substantially parallel to sternum 22. Although illustrated in FIG. 1A as being offset laterally from and extending substantially parallel to sternum 22, the distal portion 25 of lead 16 may be implanted at other locations, such as over sternum 22, offset to the right or left of sternum 22, angled laterally from sternum 22 toward the left or the right, or the like. Alternatively, lead 16 may be placed along other subcutaneous or submuscular paths. The path of extra-cardiovascular lead 16 may depend on the location of ICD 14, the arrangement and position of electrodes carried by the lead body 18, and/or other factors. The techniques disclosed herein are not limited to a particular path of lead 16 or final locations of electrodes 24, 26, 28 and 30.

Electrical conductors (not illustrated) extend through one or more lumens of the elongated lead body 18 of lead 16 from the lead connector at the proximal lead end 27 to electrodes 24, 26, 28, and 30 located along the distal portion 25 of the lead body 18. The elongated electrical conductors contained within the lead body 18, which may be separate respective insulated conductors within the lead body 18, are each electrically coupled with respective defibrillation electrodes 24 and 26 and pace/sense electrodes 28 and 30. The respective conductors electrically couple the electrodes 24, 26, 28, and 30 to circuitry, such as a therapy delivery circuit and/or a sensing circuit, of ICD 14 via connections in the connector assembly 17, including associated electrical feedthroughs crossing housing 15. The electrical conductors transmit therapy from a therapy delivery circuit within ICD 14 to one or more of defibrillation electrodes 24 and 26 and/or pace/sense electrodes 28 and 30 and transmit sensed electrical signals produced by the patient's heart 8 from one or more of defibrillation electrodes 24 and 26 and/or pace/sense electrodes 28 and 30 to the sensing circuit within ICD 14.

The lead body 18 of lead 16 may be formed from a non-conductive material, including silicone, polyurethane, fluoropolymers, mixtures thereof, and/or other appropriate materials, and shaped to form one or more lumens within which the one or more conductors extend. Lead body 18 may be tubular or cylindrical in shape. In other examples, the distal portion 25 (or all of) the elongated lead body 18 may have a flat, ribbon or paddle shape. Lead body 18 may be formed having a preformed distal portion 25 that is generally straight, curving, bending, serpentine, undulating or zig-zagging.

In the example shown, lead body 18 includes a curving distal portion 25 having two "C" shaped curves, which together may resemble the Greek letter epsilon, "ε." Defibrillation electrodes 24 and 26 are each carried by one of the two respective C-shaped portions of the lead body distal portion 25. The two C-shaped curves are seen to extend or curve in the same direction away from a central axis of lead body 18, along which pace/sense electrodes 28 and 30 are positioned. Pace/sense electrodes 28 and 30 may, in some instances, be approximately aligned with the central axis of the straight, proximal portion of lead body 18 such that mid-points of defibrillation electrodes 24 and 26 are laterally offset from pace/sense electrodes 28 and 30.

Other examples of extra-cardiovascular leads including one or more defibrillation electrodes and one or more pacing and sensing electrodes carried by curving, serpentine, undulating or zig-zagging distal portion of the lead body 18 that may be implemented with the techniques described herein are generally disclosed in pending U.S. Pat. Publication No. 2016/0158567 (Marshall, et al.), incorporated herein by reference in its entirety. The techniques disclosed herein are not limited to any particular lead body design, however. In other examples, lead body 18 is a flexible elongated lead body without any pre-formed shape, bends or curves.

ICD 14 analyzes the cardiac electrical signals received from one or more sensing electrode vectors to monitor for abnormal rhythms, such as bradycardia, ventricular tachycardia (VT) or ventricular fibrillation (VF). ICD 14 may analyze the heart rate and morphology of the cardiac electrical signals to monitor for tachyarrhythmia in accordance with any of a number of tachyarrhythmia detection techniques. Example techniques for detecting a tachyarrhythmia are described in conjunction with the flow charts presented herein.

ICD 14 generates and delivers electrical stimulation therapy in response to detecting a tachyarrhythmia (e.g., VT or VF) using a therapy delivery electrode vector which may be selected from any of the available electrodes 24, 26, 28 30 and/or housing 15. ICD 14 may deliver ATP in response to VT detection and in some cases may deliver ATP prior to a CV/DF shock or during high voltage capacitor charging in an attempt to avert the need for delivering a CV/DF shock. If ATP does not successfully terminate VT or when VF is detected, ICD 14 may deliver one or more CV/DF shocks via one or both of defibrillation electrodes 24 and 26 and/or housing 15. ICD 14 may deliver the CV/DF shocks using electrodes 24 and 26 individually or together as a cathode (or anode) and with the housing 15 as an anode (or cathode). ICD 14 may generate and deliver other types of electrical stimulation pulses such as post-shock pacing pulses or bradycardia pacing pulses using a pacing electrode vector that includes one or more of the electrodes 24, 26, 28, and 30 and the housing 15 of ICD 14.

ICD 14 is shown implanted subcutaneously on the left side of patient 12 along the ribcage 32. ICD 14 may, in some instances, be implanted between the left posterior axillary line and the left anterior axillary line of patient 12. ICD 14 may, however, be implanted at other subcutaneous or submuscular locations in patient 12. For example, ICD 14 may be implanted in a subcutaneous pocket in the pectoral region. In this case, lead 16 may extend subcutaneously or submuscularly from ICD 14 toward the manubrium of sternum 22 and bend or turn and extend inferiorly from the manubrium to the desired location subcutaneously or submuscularly. In yet another example, ICD 14 may be placed abdominally. Lead 16 may be implanted in other extra-cardiovascular locations as well. For instance, as described with respect to FIGS. 2A-2C, the distal portion 25 of lead 16 may be implanted underneath the sternum/ribcage in the substernal space. FIGS. 1A and 1B are illustrative in nature and should not be considered limiting of the practice of the techniques disclosed herein.

An external device 40 is shown in telemetric communication with ICD 14 by a communication link 42. External device 40 may include a processor 52, memory 53, display 54, user interface 56 and telemetry unit 58. Processor 52 controls external device operations and processes data and signals received from ICD 14. Display 54, which may include a graphical user interface, displays data and other information to a user for reviewing ICD operation and programmed parameters as well as cardiac electrical signals retrieved from ICD 14.

User interface 56 may include a mouse, touch screen, key pad or the like to enable a user to interact with external device 40 to initiate a telemetry session with ICD 14 for retrieving data from and/or transmitting data to ICD 14, including programmable parameters for controlling cardiac event sensing and therapy delivery. Telemetry unit 58 includes a transceiver and antenna configured for bidirectional communication with a telemetry circuit included in ICD 14 and is configured to operate in conjunction with processor 52 for sending and receiving data relating to ICD functions via communication link 42.

Communication link 42 may be established between ICD 14 and external device 40 using a radio frequency (RF) link such as BLUETOOTH®, Wi-Fi, or Medical Implant Communication Service (MICS) or other RF or communication frequency bandwidth or communication protocols. Data stored or acquired by ICD 14, including physiological signals or associated data derived therefrom, results of device diagnostics, and histories of detected rhythm episodes and delivered therapies, may be retrieved from ICD 14 by external device 40 following an interrogation command.

External device 40 may be embodied as a programmer used in a hospital, clinic or physician's office to retrieve data from ICD 14 and to program operating parameters and algorithms in ICD 14 for controlling ICD functions. External device 40 may alternatively be embodied as a home monitor or hand held device. External device 40 may be used to program cardiac signal sensing parameters, cardiac rhythm detection parameters and therapy control parameters used by ICD 14. At least some control parameters used in detecting noise according to techniques disclosed herein may be programmed into ICD 14 using external device 40 in some examples.

Figure 2A:
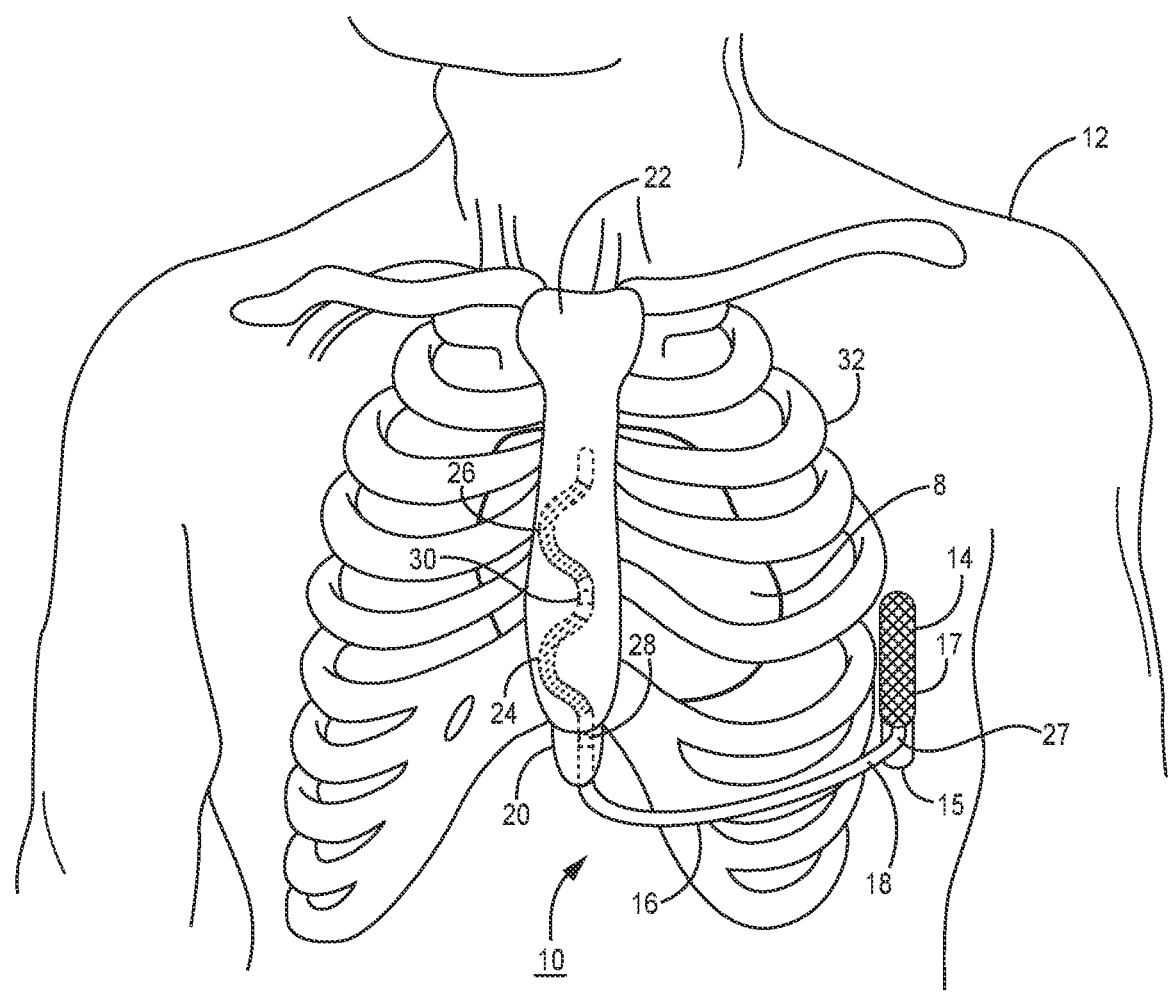
FIGS. 2A-2C are conceptual diagrams of a patient implanted with an extra-cardiovascular ICD system in a different implant configuration than the arrangement shown in FIGS. 1A-1B.
Figure 2B:
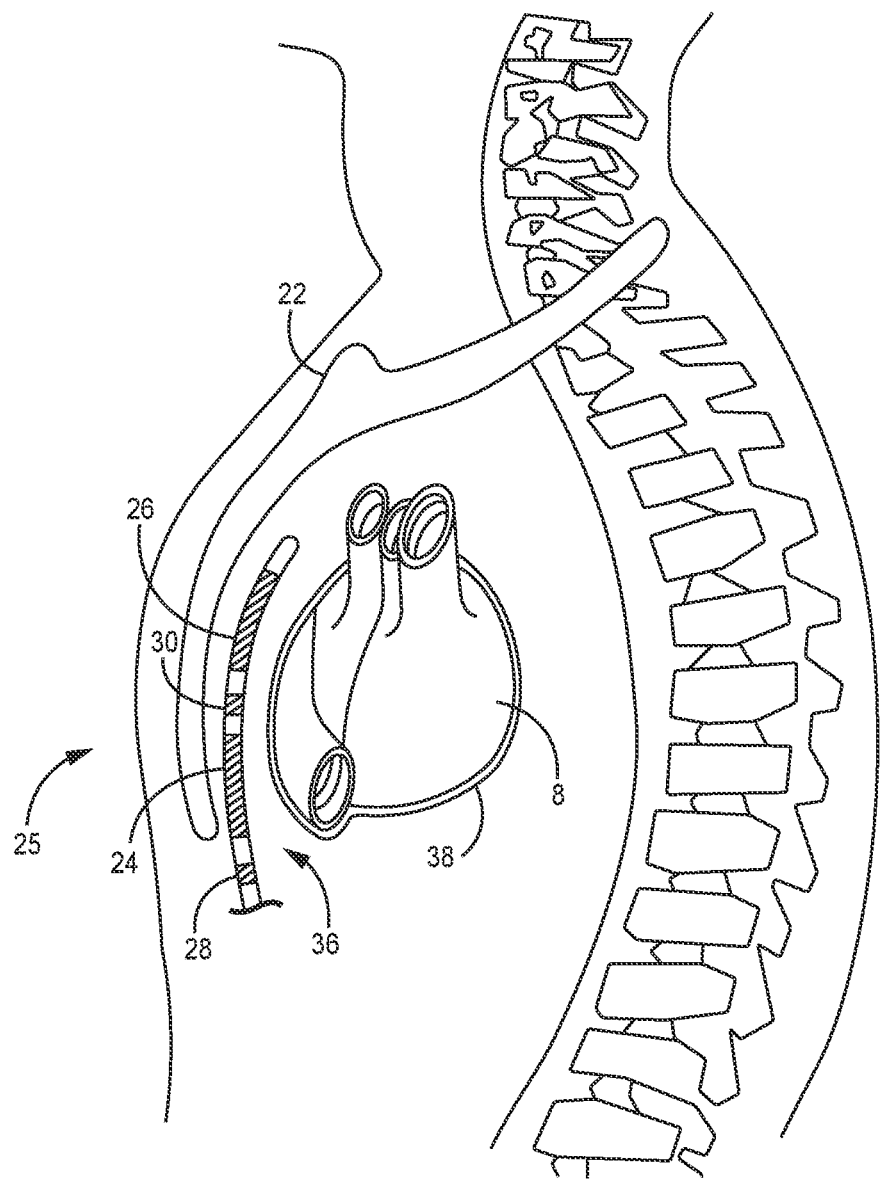
Figure 2C:
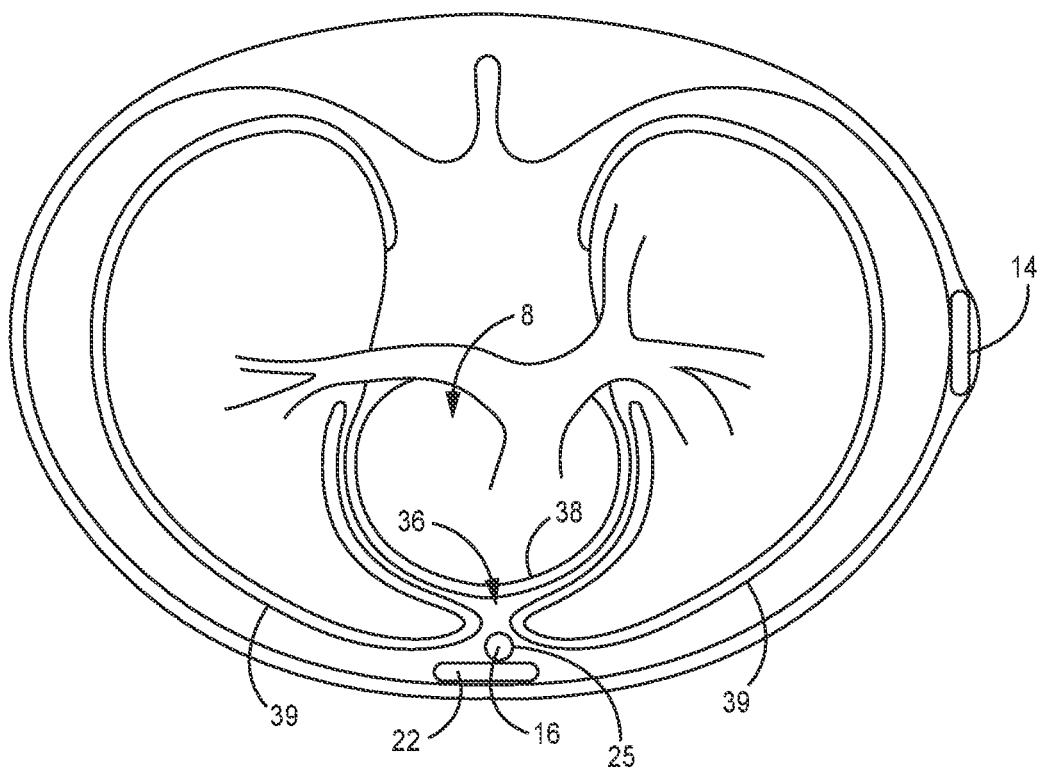

FIGS. 2A-2C are conceptual diagrams of patient 12 implanted with extra-cardiovascular ICD system 10 in a different implant configuration than the arrangement shown in FIGS. 1A-1B. FIG. 2A is a front view of patient 12 implanted with ICD system 10. FIG. 2B is a side view of patient 12 implanted with ICD system 10. FIG. 2C is a transverse view of patient 12 implanted with ICD system 10. In this arrangement, extra-cardiovascular lead 16 of system 10 is implanted at least partially underneath sternum 22 of patient 12. Lead 16 extends subcutaneously or submuscularly from ICD 14 toward xiphoid process 20 and at a location near xiphoid process 20 bends or turns and extends superiorly within anterior mediastinum 36 in a substernal position.

Anterior mediastinum 36 may be viewed as being bounded laterally by pleurae 39, posteriorly by pericardium 38, and anteriorly by sternum 22 (see FIG. 2C). The distal portion 25 of lead 16 may extend along the posterior side of sternum 22 substantially within the loose connective tissue and/or substernal musculature of anterior mediastinum 36. A lead implanted such that the distal portion 25 is substantially within anterior mediastinum 36, may be referred to as a "substernal lead."

In the example illustrated in FIGS. 2A-2C, lead 16 is located substantially centered under sternum 22. In other instances, however, lead 16 may be implanted such that it is offset laterally from the center of sternum 22. In some instances, lead 16 may extend laterally such that distal portion 25 of lead 16 is underneath/below the ribcage 32 in addition to or instead of sternum 22. In other examples, the distal portion 25 of lead 16 may be implanted in other extra-cardiovascular, intra-thoracic locations, including the pleural cavity or around the perimeter of and adjacent to the pericardium 38 of heart 8.

In the various example implant locations of extracardiovascular lead 16 and electrodes 24, 26, 28 and 30, cardiac signals sensed by ICD 14 may be contaminated by skeletal muscle myopotentials and/or environmental EMI. In some cases, the repetitive motion or sustained muscle contractions may produce episodes of myopotential noise pulses contaminated the cardiac electrical signal sensed by ICD 14. Some noise pulses may be oversensed as cardiac events, e.g., R-waves, resulting in a false heart rate being determined. In some instances, the noise may go undetected by a noise detection algorithm, even when some noise pulses are oversensed as cardiac events. If the noise detection algorithm does not detect the noise, but some noise pulses are being oversensed as cardiac events, the heart rate may be overestimated. A false tachyarrhythmia detection may be made, or bradycardia pacing may be withheld when it is actually needed. When the noise is not detected by the noise detection algorithm, falsely sensed cardiac events may go unchecked. Accordingly, the techniques disclosed herein provide improvements in non-cardiac noise detection by including a gain adjustment that may be used to increase the amplitude of noise pulses in the cardiac electrical signal to allow the noise pulses to be more readily detected as described below. The increased gain signal may be used for detecting noise without altering the gain of a signal used for sensing cardiac events. In this way, noise pulses present in the cardiac electrical signal may be more reliably detected and identified as noise so that corrective action may be taken if a noise pulse is falsely sensed (oversensed) as a cardiac event.

Figure 3:
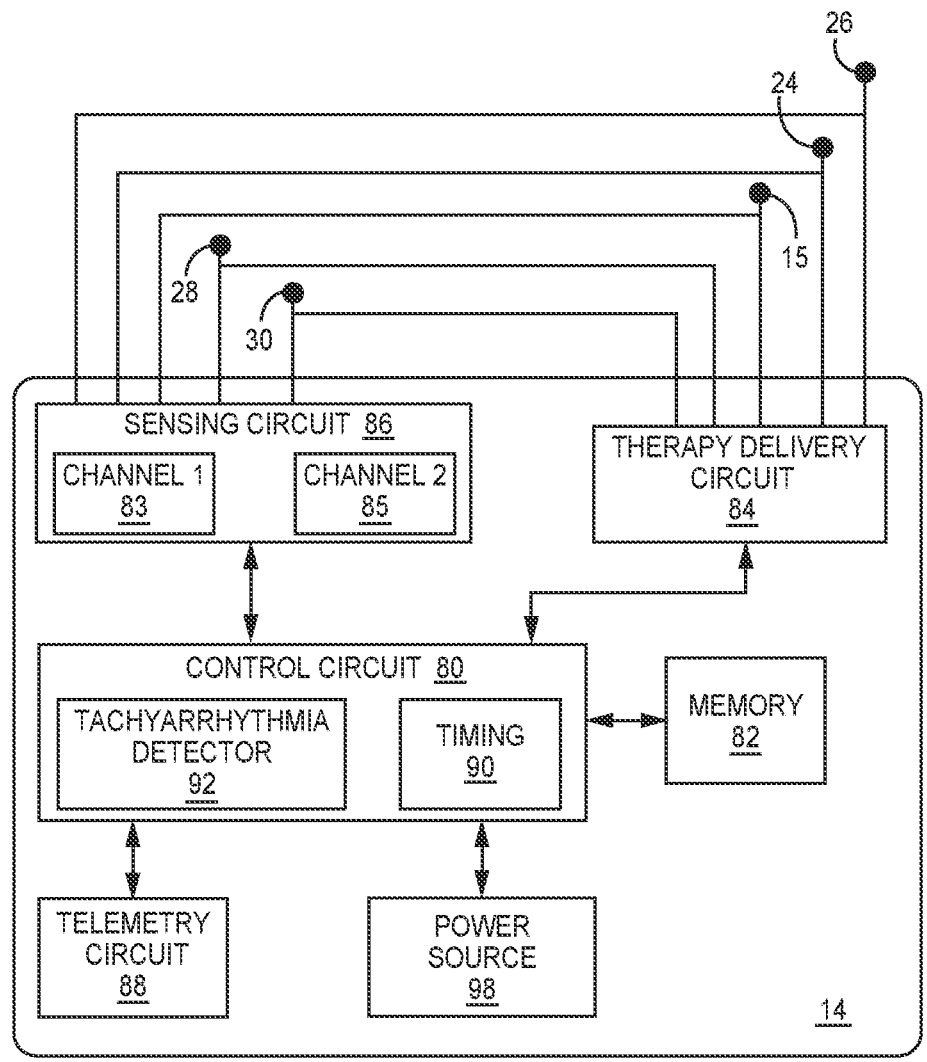
FIG. 3 is a conceptual diagram of an ICD according to one example.

FIG. 3 is a conceptual diagram of ICD 14 according to one example. The electronic circuitry enclosed within housing 15 (shown schematically as an electrode in FIG. 3) includes software, firmware and hardware that cooperatively monitor cardiac electrical signals, determine when an electrical stimulation therapy is necessary, and deliver therapy as needed according to programmed therapy delivery algorithms and control parameters. ICD 14 may be coupled to an extra-cardiovascular lead, such as lead 16 carrying extra-cardiovascular electrodes 24, 26, 28, and 30, for delivering electrical stimulation pulses to the patient's heart and for sensing cardiac electrical signals.

ICD 14 includes a control circuit 80, memory 82, therapy delivery circuit 84, cardiac electrical signal sensing circuit 86, and telemetry circuit 88. A power source 98 provides power to the circuitry of ICD 14, including each of the components 80, 82, 84, 86, and 88 as needed. Power source 98 may include one or more energy storage devices, such as one or more rechargeable or non-rechargeable batteries. The connections between power source 98 and each of the other components 80, 82, 84, 86 and 88 are to be understood from the general block diagram of FIG. 3, but are not shown for the sake of clarity. For example, power source 98 may be coupled to one or more charging circuits included in therapy delivery circuit 84 for charging holding capacitors included in therapy delivery circuit 84 that are discharged at appropriate times under the control of control circuit 80 for producing electrical pulses according to a therapy protocol. Power source 98 is also coupled to components of cardiac electrical signal sensing circuit 86, such as sense amplifiers, analog-to-digital converters, switching circuitry, etc. as needed.

The circuits shown in FIG. 3 represent functionality included in ICD 14 and may include any discrete and/or integrated electronic circuit components that implement analog and/or digital circuits capable of producing the functions attributed to ICD 14 herein. Functionality associated with one or more circuits may be performed by separate hardware, firmware or software components, or integrated within common hardware, firmware or software components. For example, cardiac event sensing and detection of noise for rejecting sensed events or withholding detection of a tachyarrhythmia based on cardiac event intervals may be performed cooperatively by sensing circuit 86 and control circuit 80 and may include operations implemented in a processor or other signal processing circuitry included in control circuit 80 executing instructions stored in memory 82 and control signals such as blanking and timing intervals and sensing threshold amplitude signals sent from control circuit 80 to sensing circuit 86.

The various circuits of ICD 14 may include an application specific integrated circuit (ASIC), an electronic circuit, a processor (shared, dedicated, or group) and memory that execute one or more software or firmware programs, a combinational logic circuit, state machine, or other suitable components or combinations of components that provide the described functionality. The particular form of software, hardware and/or firmware employed to implement the functionality disclosed herein will be determined primarily by the particular system architecture employed in the ICD and by the particular detection and therapy delivery methodologies employed by the ICD. Providing software, hardware, and/or firmware to accomplish the described functionality in the context of any modern implantable cardiac device system, given the disclosure herein, is within the abilities of one of skill in the art.

Memory 82 may include any volatile, non-volatile, magnetic, or electrical non-transitory computer readable storage media, such as random access memory (RAM), read-only memory (ROM), non-volatile RAM (NVRAM), electrically-erasable programmable ROM (EEPROM), flash memory, or any other memory device. Furthermore, memory 82 may include non-transitory computer readable media storing instructions that, when executed by one or more processing circuits, cause control circuit 80 and/or other ICD components to perform various functions attributed to ICD 14 or those ICD components. The non-transitory computer-readable media storing the instructions may include any of the media listed above.

Control circuit 80 communicates, e.g., via a data bus, with therapy delivery circuit 84 and sensing circuit 86 for sensing cardiac electrical activity, detecting cardiac rhythms, and controlling delivery of cardiac electrical stimulation therapies in response to sensed cardiac signals. Therapy delivery circuit 84 and sensing circuit 86 are electrically coupled to electrodes 24, 26, 28, 30 carried by lead 16 and the housing 15, which may function as a common or ground electrode or as an active can electrode for delivering CV/DF shock pulses or cardiac pacing pulses.

Cardiac electrical signal sensing circuit 86 (also referred to herein as "sensing circuit" 86) may be selectively coupled to electrodes 28, 30 and/or housing 15 in order to monitor electrical activity of the patient's heart. Sensing circuit 86 may additionally be selectively coupled to defibrillation electrodes 24 and/or 26 for use in a sensing electrode vector together or in combination with one or more of electrodes 28, 30 and/or housing 15. Sensing circuit 86 may be enabled to selectively receive cardiac electrical signals from at least two sensing electrode vectors from the available electrodes 24, 26, 28, 30, and housing 15 in some examples. At least two cardiac electrical signals from two different sensing electrode vectors may be received simultaneously by sensing circuit 86 in some examples. Sensing circuit 86 may monitor one or both of the cardiac electrical signals simultaneously for sensing cardiac electrical events and/or producing digitized cardiac signal waveforms for analysis by control circuit 80. For example, sensing circuit 86 may include switching circuitry for selecting which of electrodes 24, 26, 28, 30, and housing 15 are coupled to a first sensing channel 83 and which electrodes are coupled to a second sensing channel 85 of sensing circuit 86.

Each sensing channel 83 and 85 may be configured to amplify, filter and digitize the cardiac electrical signal received from selected electrodes coupled to the respective sensing channel to improve the signal quality for detecting cardiac electrical events, such as R-waves or performing other signal analysis. The cardiac event detection circuitry within sensing circuit 86 may include one or more sense amplifiers, filters, rectifiers, threshold detectors, comparators, analog-to-digital converters (ADCs), timers or other analog or digital components as described further in conjunction with FIG. 4. A cardiac event sensing threshold may be automatically adjusted by sensing circuit 86 under the control of control circuit 80, based on timing intervals and sensing threshold values determined by control circuit 80, stored in memory 82, and/or controlled by hardware, firmware and/or software of control circuit 80 and/or sensing circuit 86.

Upon detecting a cardiac event based on a sensing threshold crossing, first sensing channel 83 may produce a sensed event signal, such as an R-wave sensed event signal, that is passed to control circuit 80. The sensed event signal is used by control circuit 80 to trigger storage of a time segment of a cardiac electrical signal for processing and analysis for detecting noise in the cardiac electrical signal as described below. In some examples, sensing circuit 86 senses at least one cardiac electrical signal received by a sensing electrode vector selected from the available electrodes, e.g., electrodes 24, 26, 28, 30 and housing 15, for detecting R-waves and buffering multiple cardiac electrical signal segments, where each cardiac electrical signal segment corresponds to a detected R-wave, for processing and analysis for detecting noise. A single cardiac electrical signal sensed by first sensing channel 83 may be used for both R-wave detection and analysis of cardiac electrical signal segments for noise detection. In other examples, R-waves are detected from the first cardiac electrical signal sensed by the first sensing channel 83 and segments of a second cardiac electrical signal sensed by the second sensing channel 85 may be buffered, with each segment corresponding to an R-wave sensed from the first cardiac electrical signal. Noise detection may be based on the analysis of the second cardiac electrical signal segments. The second cardiac electrical signal may be received via a sensing electrode pair coupled to the second sensing channel 85 different than the sensing electrode pair coupled to the first sensing channel 83 for sensing than the first cardiac electrical signal and/or may be received by the same sensing electrode pair but processed differently, e.g., filtered differently, by the second sensing channel 85 to produce a second cardiac electrical signal sensed by sensing circuit 86 different than the first cardiac electrical signal.

Memory 82 may be configured to store a predetermined number of cardiac electrical signal segments in a circulating buffer under the control of control circuit 80, e.g., at least one, two, three or other number of cardiac electrical signal segments. Each segment may be written to memory 82 over a time interval extending before and after an R-wave sensed event signal produced by the first sensing channel 83. Control circuit 80 may access stored cardiac electrical signal segments when confirmation of R-waves sensed by the first sensing channel 83 is required based on the detection of a predetermined number of tachyarrhythmia intervals, which may precede tachyarrhythmia detection. In some examples, an R-wave sensed by the first sensing channel 83 may be rejected when an associated cardiac electrical signal segment buffered from the second sensing channel 85 (including the time of the sensed R-wave) is classified as a noise segment. In other examples, the sensed R-wave may be used to determine an RRI that may be counted as a tachyarrhythmia interval but if a tachyarrhythmia detection criterion is satisfied, tachyarrhythmia detection may be withheld when a threshold number of cardiac electrical signal segments are classified as noise segments. Methods for classifying a cardiac electrical signal segment as a noise segment are described below, e.g., in conjunction with FIGS. 5-8.

The R-wave sensed event signals are also used by control circuit 80 for determining RRIs for detecting tachyarrhythmia and determining a need for therapy. An RRI is the time interval between two consecutively sensed R-waves and may be determined between consecutive R-wave sensed event signals received by control circuit 80 from sensing circuit 86. For example, control circuit 80 may include a timing circuit 90 for determining RRIs between consecutive R-wave sensed event signals received from sensing circuit 86 and for controlling various timers and/or counters used to control the timing of therapy delivery by therapy delivery circuit 84. Timing circuit 90 may additionally set time windows such as morphology template windows, morphology analysis windows or perform other timing related functions of ICD 14 including synchronizing cardioversion shocks or other therapies delivered by therapy delivery circuit 84 with sensed cardiac events.

Control circuit 80 is also shown to include a tachyarrhythmia detector 92 configured to analyze signals received from sensing circuit 86 for detecting tachyarrhythmia. Tachyarrhythmia detector 92 may detect tachyarrhythmia based on cardiac events detected from a sensed cardiac electrical signal meeting tachyarrhythmia criteria, such as a threshold number of detected cardiac events occurring at a tachyarrhythmia interval. In some examples, a tachyarrhythmia detection based on the threshold number of detected cardiac events each occurring at a tachyarrhythmia interval may be rejected based on non-cardiac noise being detected using the techniques disclosed herein. Tachyarrhythmia detector 92 may be implemented in control circuit 80 as hardware, software and/or firmware that processes and analyzes signals received from sensing circuit 86 for detecting VT and/or VF. In some examples, the timing of R-wave sense event signals received from sensing circuit 86 is used by timing circuit 90 to determine RRIs between sensed event signals. Tachyarrhythmia detector 92 may include comparators and counters for counting RRIs determined by timing circuit 90 that fall into various rate detection zones for determining a ventricular rate or performing other rate- or interval-based assessment of R-wave sensed event signals for detecting and discriminating VT and VF.

For example, tachyarrhythmia detector 92 may compare the RRIs determined by timing circuit 90 to one or more tachyarrhythmia detection interval zones, such as a tachycardia detection interval zone and a fibrillation detection interval zone. RRIs falling into a detection interval zone are counted by a respective VT interval counter or VF interval counter and in some cases in a combined VT/VF interval counter included in tachyarrhythmia detector 92. The VF detection interval threshold may be set to 300 to 350 milliseconds (ms), as examples. For instance, if the VF detection interval is set to 320 ms, RRIs that are less than 320 ms are counted by the VF interval counter. When VT detection is enabled, the VT detection interval may be programmed to be in the range of 350 to 420 ms, or 400 ms as an example. In order to detect VT or VF, the respective VT or VF interval counter is required to reach a threshold "number of intervals to detect" (NID).

As an example, the NID to detect VT may require that the VT interval counter reaches 32 VT intervals counted out of the most recent 32 consecutive RRIs. The NID required to detect VF may be programmed to 18 VF intervals out of the most recent 24 consecutive RRIs or 30 VF intervals out 40 consecutive RRIs, as examples. When a VT or VF interval counter reaches an NID threshold, a ventricular tachyarrhythmia may be detected by tachyarrhythmia detector 92. The NID may be programmable and range from as low as 12 to as high as 40, with no limitation intended. VT or VF intervals may be detected consecutively or non-consecutively out of the specified number of most recent RRIs. In some cases, a combined VT/VF interval counter may count both VT and VF intervals and detect a tachyarrhythmia episode based on the fastest intervals detected when a specified NID is reached.

Tachyarrhythmia detector 92 may be configured to perform other signal analysis for determining if other detection criteria are satisfied before detecting VT or VF, such as R-wave morphology criteria, onset criteria, and noise and oversensing rejection criteria. Examples of parameters that may be determined from cardiac electrical signals received from sensing circuit 86 for detecting noise that may cause withholding of a VT or VF detection are described below.

To support these additional analyses, sensing circuit 86 may pass a digitized electrocardiogram (ECG) signal to control circuit 80 for morphology analysis performed by tachyarrhythmia detector 92 for detecting and discriminating heart rhythms. A cardiac electrical signal from the selected sensing vector, e.g., from first sensing channel 83 and/or the second sensing channel 85, may be passed through a filter and amplifier, provided to a multiplexer and thereafter converted to a multi-bit digital signal by an analog-to-digital converter, all included in sensing circuit 86, for storage in memory 82. Memory 82 may include one or more circulating buffers to temporarily store digital cardiac electrical signal segments for analysis performed by control circuit 80. Control circuit 80 may be a microprocessor-based controller that employs digital signal analysis techniques to characterize the digitized signals stored in memory 82 to recognize and classify the patient's heart rhythm employing any of numerous signal processing methodologies for analyzing cardiac signals and cardiac event waveforms, e.g., R-waves. As described below, processing and analysis of digitized signals may include determining signal features for detecting noise present in the cardiac electrical signal(s). When noise is detected, a tachyarrhythmia detection based on RRIs may be withheld to inhibit a tachyarrhythmia therapy. Alternatively, a tachyarrhythmia therapy may be withheld in response to a tachyarrhythmia detection made when noise is also detected.

Therapy delivery circuit 84 includes charging circuitry, one or more charge storage devices such as one or more high voltage capacitors and/or low voltage capacitors, and switching circuitry that controls when the capacitor(s) are discharged across a selected pacing electrode vector or CV/DF shock vector. Charging of capacitors to a programmed pulse amplitude and discharging of the capacitors for a programmed pulse width may be performed by therapy delivery circuit 84 according to control signals received from control circuit 80. Control circuit 80 may include various timers or counters that control when cardiac pacing pulses are delivered. For example, timing circuit 90 may include programmable digital counters set by a microprocessor of the control circuit 80 for controlling the basic pacing time intervals associated with various pacing modes or ATP sequences delivered by ICD 14. The microprocessor of control circuit 80 may also set the amplitude, pulse width, polarity or other characteristics of the cardiac pacing pulses, which may be based on programmed values stored in memory 82.

In response to detecting VT or VF, control circuit 80 may schedule a therapy and control therapy delivery circuit 84 to generate and deliver the therapy, such as ATP and/or CV/DF therapy. Therapy can be generated by initiating charging of high voltage capacitors via a charging circuit, both included in therapy delivery circuit 84. Charging is controlled by control circuit 80 which monitors the voltage on the high voltage capacitors, which is passed to control circuit 80 via a charging control line. When the voltage reaches a predetermined value set by control circuit 80, a logic signal is generated on a capacitor full line and passed to therapy delivery circuit 84, terminating charging. A CV/DF pulse is delivered to the heart under the control of the timing circuit 90 by an output circuit of therapy delivery circuit 84 via a control bus. The output circuit may include an output capacitor through which the charged high voltage capacitor is discharged via switching circuitry, e. g., an H-bridge, which determines the electrodes used for delivering the cardioversion or defibrillation pulse and the pulse wave shape.

In some examples, the high voltage therapy circuit configured to deliver CV/DF shock pulses can be controlled by control circuit 80 to deliver pacing pulses, e.g., for delivering ATP, post shock pacing pulses or ventricular pacing pulses. In other examples, therapy delivery circuit 84 may include a low voltage therapy circuit for generating and delivering pacing pulses for a variety of pacing needs.

It is recognized that the methods disclosed herein for detecting noise may be implemented in a medical device that is used for monitoring cardiac electrical signals by sensing circuit 86 and control circuit 80 without having therapy delivery capabilities or in a pacemaker that monitors cardiac electrical signals and delivers cardiac pacing therapies by therapy delivery circuit 84, without high voltage therapy capabilities, such as cardioversion/defibrillation shock capabilities.

Control parameters utilized by control circuit 80 for sensing cardiac events and controlling therapy delivery may be programmed into memory 82 via telemetry circuit 88. Telemetry circuit 88 includes a transceiver and antenna for communicating with external device 40 (shown in FIG. 1A) using RF communication or other communication protocols as described above. Under the control of control circuit 80, telemetry circuit 88 may receive downlink telemetry from and send uplink telemetry to external device 40.

Figure 4:
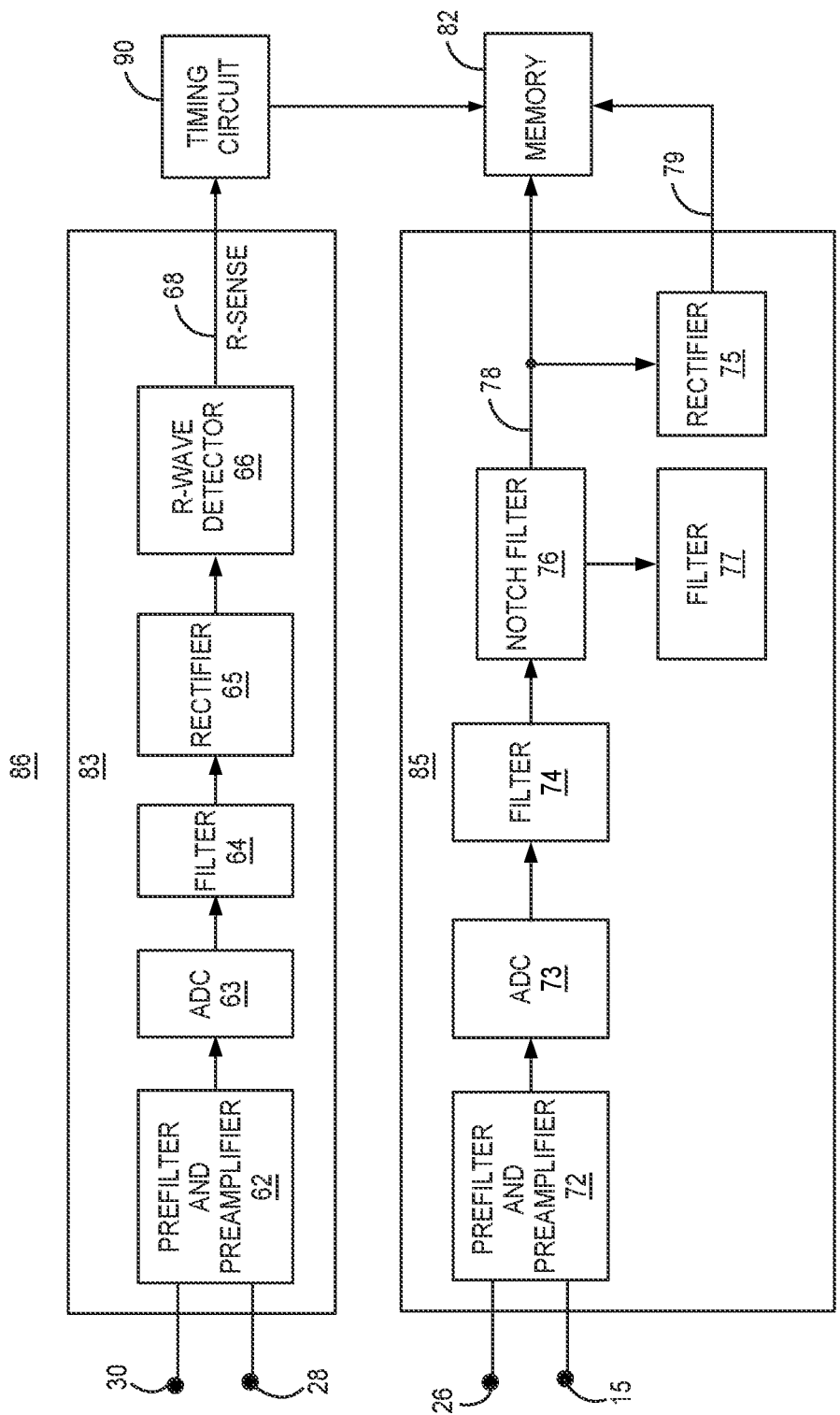
FIG. 4 is a diagram of circuitry that may be included in a sensing circuit of the ICD of FIG. 3.

FIG. 4 is a diagram of circuitry included in sensing circuit 86 having first sensing channel 83 and second sensing channel 85 according to one example. First sensing channel 83 may be selectively coupled via switching circuitry included in sensing circuit 86 to a first sensing electrode vector including at least one electrode carried by extra-cardiovascular lead 16 for receiving a first cardiac electrical signal. In some examples, first sensing channel 83 may be coupled to a sensing electrode vector that is a short bipole, having a relatively shorter inter-electrode distance or spacing than the second electrode vector coupled to second sensing channel 85. First sensing channel 83 may be coupled to a sensing electrode vector that is approximately vertical (when the patient is in an upright position) or approximately aligned with the cardiac axis to increase the likelihood of a relatively high R-wave signal amplitude relative to P-wave signal amplitude. In one example, the first sensing electrode vector may include pace/sense electrodes 28 and 30. In other examples, the first sensing electrode vector coupled to sensing channel 83 may include a defibrillation electrode 24 and/or 26, e.g., a sensing electrode vector between pace/sense electrode 28 and defibrillation electrode 24 or between pace/sense electrode 30 and either of defibrillation electrodes 24 or 26. In still other examples, the first sensing electrode vector may be between defibrillation electrodes 24 and 26.

Sensing circuit 86 includes second sensing channel 85 for sensing a second cardiac electrical signal in some examples. For instance, second sensing channel 85 may receive a raw cardiac electrical signal from a second sensing electrode vector, for example from a vector that includes one electrode 24, 26, 28 or 30 carried by lead 16 paired with housing 15. Second sensing channel 85 may be selectively coupled to other sensing electrode vectors, which may form a relatively longer bipole having an inter-electrode distance or spacing that is greater than the sensing electrode vector coupled to first sensing channel 83 in some examples. The second sensing electrode vector may be, but not necessarily, approximately orthogonal to the first channel sensing electrode vector in some cases. For instance, defibrillation electrode 26 and housing 15 may be coupled to second sensing channel 85 to provide the second cardiac electrical signal. As described below, the second cardiac electrical signal received by second sensing channel 85 via a long bipole may be used by control circuit 80 for analysis and detection of noise. The long bipole coupled to second sensing channel 85 may provide a relatively far-field or more global cardiac signal compared to the relatively shorter bipole coupled to the first sensing channel. In other examples, any vector selected from the available electrodes, e.g., electrodes 24, 26, 28, 30 and/or housing 15, may be included in a sensing electrode vector coupled to second sensing channel 85. The sensing electrode vectors coupled to first sensing channel 83 and second sensing channel 85 may be different sensing electrode vectors, which may have no common electrodes or only one common electrode but not both.

In other examples, however, the sensing electrode vectors coupled to the first sensing channel 83 and the second sensing channel 85 may be the same sensing electrode vector. The two sensing channels 83 and 85 may include different filters, amplifiers, or other signal processing circuitry such that two different signals are sensed by the respective sensing channels 83 and 85 and different analyses may be performed on the two signals. For example, the first sensing channel 83 may sense a first cardiac electrical signal by filtering and processing the received cardiac electrical signal for detecting R-waves in response to an R-wave sensing threshold crossing for determining RRIs. The second sensing channel 85 may sense a second cardiac electrical signal different than the first by filtering and processing the received cardiac electrical signal for passing signal segments to control circuit 80 for analysis for noise detection. The first sensing channel 83 may apply relatively narrower band pass filtering, and the second sensing channel 85 may apply relatively wider band pass filtering and notch filtering to provide two different sensed cardiac electrical signals, received via the same sensing electrode vector in some examples.

In the illustrative example shown in FIG. 4, the electrical signals developed across the first sensing electrode vector, e.g., electrodes 28 and 30, are received by first sensing channel 83 and electrical signals developed across the second sensing electrode vector, e.g., electrodes 26 and housing 15, are received by second sensing channel 85. The cardiac electrical signals are provided as differential input signals to the pre-filter and pre-amplifier 62 or 72, respectively, of first sensing channel 83 and second sensing channel 85. Non-physiological high frequency and DC signals may be filtered by a low pass or bandpass filter included in each of pre-filter and pre-amplifiers 62 and 72, and high voltage signals may be removed by protection diodes included in pre-filter and pre-amplifiers 62 and 72. Pre-filter and pre-amplifiers 62 and 72 may amplify the pre-filtered signal by a gain of between 10 and 100, and in one example a gain of 17.5, and may convert the differential signal to a single-ended output signal passed to analog-to-digital converter (ADC) 63 in first sensing channel 83 and to ADC 73 in second sensing channel 85. Pre-filters and amplifiers 62 and 72 may provide anti-alias filtering and noise reduction prior to digitization.

ADC 63 and ADC 73, respectively, convert the first cardiac electrical signal from an analog signal to a first digital bit stream and the second cardiac electrical signal to a second digital bit stream. In one example, ADC 63 and ADC 73 may be sigma-delta converters (SDC), but other types of ADCs may be used. In some examples, the outputs of ADC 63 and ADC 73 may be provided to decimators (not shown), which function as digital low-pass filters that increase the resolution and reduce the sampling rate of the respective first and second cardiac electrical signals.

The digital outputs of ADC 63 and ADC 73 are each passed to respective filters 64 and 74, which may be digital bandpass filters. The bandpass filters 64 and 74 may have the same or different bandpass frequencies. For example, filter 64 may have a bandpass of approximately 13 Hz to 39 Hz for passing cardiac electrical signals such as R-waves typically occurring in this frequency range. Filter 74 of the second sensing channel 85 may have a bandpass of approximately 2.5 to 100 Hz. In some examples, second sensing channel 85 may further include a notch filter 76 to filter 60 Hz or 50 Hz noise signals.

The bandpass filtered signal in first sensing channel 83 is passed from filter 64 to rectifier 65 to produce a filtered, rectified signal. First sensing channel 83 includes an R-wave detector 66 for sensing cardiac events in response to the first cardiac electrical signal crossing an R-wave sensing threshold. R-wave detector 66 may include an auto-adjusting sense amplifier, comparator and/or other detection circuitry that compares the filtered and rectified cardiac electrical signal to an R-wave sensing threshold in real time and produces an R-wave sensed event signal 68 when the cardiac electrical signal crosses the R-wave sensing threshold outside of a post-sense blanking interval. The R-wave sensing threshold may be a multi-level sensing threshold as disclosed in commonly assigned U.S. Pat. No. 10,252,071 (Cao, et al.), incorporated herein by reference in its entirety. Briefly, the multi-level sensing threshold may have a starting sensing threshold value held for a time interval, which may be equal to a tachycardia detection interval or expected R-wave to T-wave interval, then drops to a second sensing threshold value held until a drop time interval expires, which may be 1 to 2 seconds long. The sensing threshold drops to a minimum sensing threshold, which may correspond to a programmed sensitivity sometimes referred to as the "sensing floor," after the drop time interval. In other examples, the R-wave sensing threshold used by R-wave detector 66 may be set to a starting value based on the peak amplitude determined during the most recent post-sense blanking interval and decay linearly or exponentially over time until reaching a minimum sensing threshold. The techniques described herein are not limited to a specific behavior of the sensing threshold or specific R-wave sensing techniques. Instead, other decaying, step-wise adjusted or other automatically adjusted sensing thresholds may be utilized.

The notch-filtered, digital cardiac electrical signal 78 from second sensing channel 85 may be passed to memory 82 for buffering a segment of the second cardiac electrical signal 78 in response to an R-wave sensed event signal 68 produced by the first sensing channel 83. In some examples, the buffered segment of the second cardiac electrical signal 78 is rectified by rectifier 75 before being stored in memory 82. In some cases, both the filtered, non-rectified signal 78 and the rectified signal 79 are passed to control circuit 80 and/or memory 82 for use in determining features of multiple segments of the second cardiac electrical signal, where each segment extends over a time interval that encompasses the time point of an R-wave sensed event signal produced by the first sensing channel 83.

Second sensing channel 85 may include a filter 77 in some examples. Filter 77 may be a first order derivative filter for receiving the notch filtered signal from notch filter 76 and producing a first order differential signal 81 (e.g., where the $i^{th}$ sample of the first order differential signal is the difference between the $i^{th}$ sample point of the notch filtered signal and the preceding i−1 sample point of the notch filtered signal). In other examples, a higher order differential signal may be output by derivative filter 77, e.g., second order or higher. In still other examples, derivative filter 77 may be a high pass filter with a sharp cut-off corner frequency, e.g., a 50 Hz, 60 Hz, 80 Hz or 100 Hz high pass filter as examples. Filter 77 may be configured to produce a filtered signal that removes low frequency cardiac event signals without removing higher frequency noise pulses, which may be 50 Hz or higher. The differential (or filtered) signal 81 may be buffered in memory 82 and passed to control circuit 80 for processing and analysis for detecting noise contamination presumed to be present in both of the first cardiac electrical signal 68 and the second cardiac electrical signal 78. In some examples, the differential signal 81 may be rectified by rectifier 75 before buffering in memory 82 for processing and analysis by control circuit 80. In other examples, the differential signal 81 is buffered in memory 82 without rectifying and is processed and analyzed by control circuit 80 for detecting noise contamination as described below.

Control circuit 80 is configured to detect tachyarrhythmia based on cardiac events detected from at least one cardiac electrical signal sensed by sensing circuit 86. For example, control circuit 80 may be configured to detect tachyarrhythmia when a detection threshold number of detected cardiac events each occur at a tachyarrhythmia interval. Control circuit 80 may buffer segments of a sensed cardiac electrical signal in memory 82 and retrieve stored signal segments from memory 82 for analysis when a lower threshold number of tachyarrhythmia intervals have been detected, before the NID tachyarrhythmia detection threshold is reached. In some examples, RRIs for detecting tachyarrhythmia intervals are determined from the first cardiac electrical signal sensed by first sensing channel 83, and cardiac electrical signal segments are buffered from the second cardiac electrical signal received by control circuit 80 from second sensing channel 85 for noise analysis when the lower threshold number of tachyarrhythmia intervals is detected. Analysis of the second cardiac electrical signal segments may be performed for use in detecting non-cardiac noise before the detection threshold number of tachyarrhythmia intervals (NID) is reached, as described below. In other examples, a single cardiac electrical signal sensed by sensing circuit 86 is used for sensing R-waves for determining RRIs and counting tachyarrhythmia intervals and is buffered for storing a cardiac electrical signal segments for use in detecting noise, where each buffered segment is associated with one sensed R-wave.

For instance, control circuit 80 may be configured to determine a maximum amplitude from each one of multiple, consecutive cardiac electrical signal segments for determining if signal to noise criteria are met. If so, control circuit 80 may increase the signal gain to intentionally increase the amplitude of noise pulses in the cardiac electrical signal segment. By increasing the signal gain, non-cardiac noise pulses may be more readily detected as noise. Increasing the gain improves detection of noise allowing identification of potential oversensing of noise pulses as R-waves, which can lead to tachyarrhythmia intervals being detected. One or more noise metrics may be determined from the increased gain signal for determining if noise criteria are met. When a threshold number of cardiac electrical signal segments meet noise criteria, detection of a tachyarrhythmia based on a threshold number of tachyarrhythmia intervals or other detection criterion may be withheld or rejected. In other examples, an RRI that is associated with a cardiac electrical signal segment determined to be noise contaminated may be ignored and not used in counting tachyarrhythmia intervals. Time segments of the notch-filtered, rectified signal 79 received from second sensing channel 85 may be used to detect noise segments that may result in withholding a tachyarrhythmia detection in some examples.

The configuration of sensing channels 83 and 85 as shown in FIG. 4 is illustrative in nature and should not be considered limiting of the techniques described herein. The sensing channels 83 and 85 of sensing circuit 86 may include more or fewer components than illustrated and described in FIG. 4 and some components may be shared between sensing channels 83 and 85. For example, one or more of pre-filter and pre-amplifiers 62/72, ADC 63/73, and/or filters 64/74 may be shared components between sensing channels 83 and 85 with a single, sensed signal output split to two sensing channels for subsequent processing and analysis. Sensing circuit 86 and control circuit 80 include circuitry configured to perform the functionality attributed to ICD 14 in detecting non-cardiac noise and rejecting or withholding tachyarrhythmia interval or episode detection in response to detecting non-cardiac noise as disclosed herein.

Figure 5:
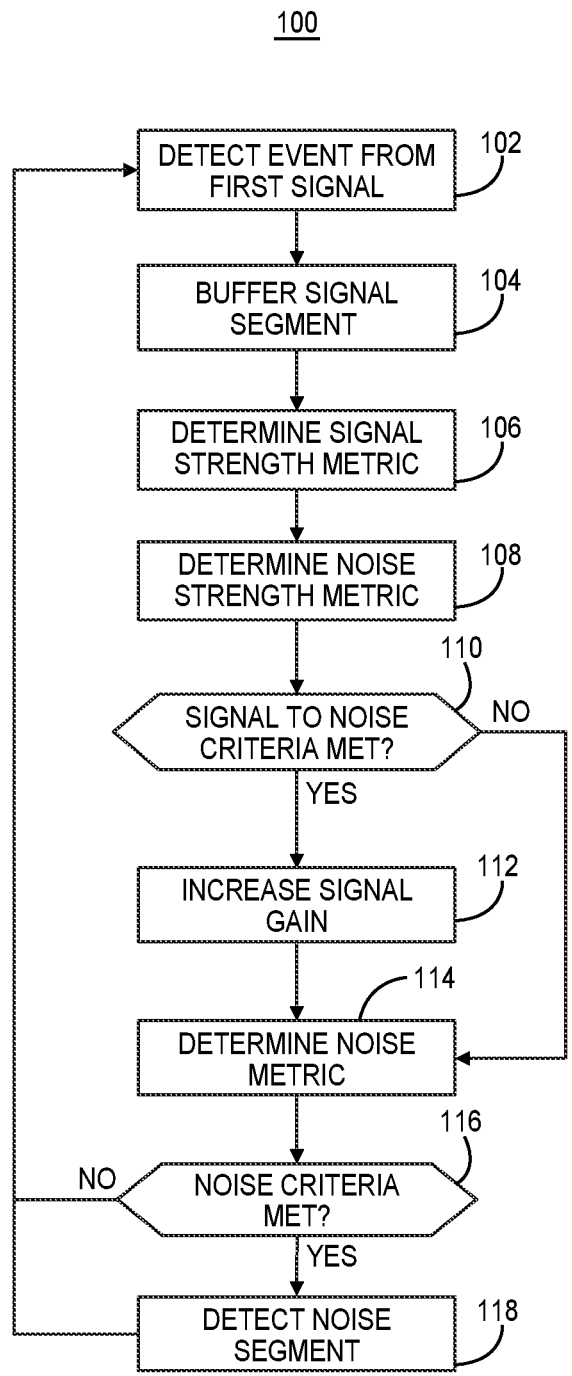
FIG. 5 is a flow chart of a method for detecting non-cardiac noise in a cardiac electrical signal by a medical device such as the ICD of FIG. 3 according to one example.

FIG. 5 is a flow chart 100 of a method for detecting non-cardiac noise in a cardiac electrical signal according to one example. In various examples presented herein, non-cardiac noise pulses, such as skeletal muscle myopotentials, may be oversensed by sensing circuit 86 as R-waves (or other cardiac event signals corresponding to depolarization/repolarization of the cardiac tissue). For example, when a noise pulse crosses an R-wave sensing threshold of R-wave detector 66 (FIG. 4), a false R-wave sensed event signal 68 may be produced at a tachyarrhythmia interval from the most recent preceding R-wave sensed event signal, leading to a VT or VF interval counter being increased. It is to be understood, however, that the techniques disclosed herein for detecting non-cardiac noise may be applied for detecting likely oversensing of noise when P-waves are being sensed by a sensing circuit of a medical device. In this case, oversensing of non-cardiac noise pulses occurs when a noise pulse in the cardiac electrical signal crosses the P-wave sensing threshold, causing the sensing circuit to produce a false P-wave sensed event signal. The false P-wave sensed event signal may be counted as a tachyarrhythmia interval, toward atrial tachyarrhythmia detection criteria being met. Furthermore, the method shown in FIG. 5 may be adapted for detecting noise in any electrical signal sensed by a medical device being used to monitor or detect electrophysiological event signals. Noise signals that may corrupt the electrical signal may be detected using the technique of flow chart 100.

At block 102, sensing circuit 86 senses a cardiac event based on a cardiac event sensing threshold crossing by a cardiac electrical signal. In some examples, the cardiac electrical signal is received by first sensing channel via a sensing electrode vector that is a relatively near field signal for increasing the likelihood of sensing cardiac events in a desired heart chamber, e.g., ventricular or atrial, without oversensing a cardiac event in the adjacent heart chamber, e.g., atrial or ventricular. In one example, cardiac events sensed at block 102 are intended to be R-waves sensed based on an R-wave sensing threshold crossing detected by the first sensing channel 83 of sensing circuit 86 as described above. In other medical applications, an electrophysiological event, e.g., corresponding to an action potential or depolarization or repolarization of excitable tissue, may be sensed from an electrical signal sensed by a medical device at block 102.

At block 104, control circuit 80 may buffer a segment of an electrical signal in memory 82 for noise analysis in response to an electrophysiological event sensed at block 102. Noise analysis may be performed by control circuit 80 to reject the sensed electrophysiological event (or reject or withhold detecting a condition based on the sensed electrophysiological event) in response to detecting noise in the buffered signal segment associated with the sensed electrophysiological event. Control circuit 80 may buffer the signal segment in memory 82 at block 104 for further analysis and processing as described below. In some examples, the buffered signal segment is from the same signal that the event was detected from at block 102, and in other examples the buffered signal segment is a different signal, e.g., sensed using a different sensing electrode pair and/or produced by sensing circuit 84 using different filtering, amplification, etc. than the first signal.

The buffered segment may be a cardiac electrical signal received from the second sensing channel 85, and may be notch-filtered to attenuate 50-60 Hz noise. In some examples, the second sensing channel 85 receives a cardiac electrical signal via a different sensing electrode vector for sensing a second cardiac electrical signal different than the first cardiac electrical signal used at block 102 for sensing cardiac events. In other examples, the same sensing electrode vector is used for receiving a single cardiac electrical signal used for both sensing cardiac events and buffering cardiac electrical signal segments used for noise detection. When the same sensing electrode vector is used, different filtering or other signal processing may be used for producing a first sensed cardiac electrical signal for detecting cardiac events at block 102 and producing a second sensed cardiac electrical signal for buffering signal segments at block 104 for noise analysis.

A segment of the second cardiac electrical signal may be buffered over a predetermined time interval that encompasses a time point at which a cardiac event was sensed from the first cardiac electrical signal. For example, in response to an R-wave sensed event signal 68 received from the first sensing channel 83 (see FIG. 4), control circuit 80 may buffer a time segment of the second cardiac electrical signal 78 (and the rectified signal 79 in some examples) from the second sensing channel 85 in memory 82. The time segment may extend from a time point earlier than the time of one R-wave sensing threshold crossing to a time point later than the R-wave sensing threshold crossing that caused the first sensing channel 83 to generate an R-wave sensed event signal 68. The time segment may be 300 to 500 ms in duration, e.g., 360 ms in duration, including sample points preceding and following the one R-wave sensed event signal. For instance, as described in conjunction with FIG. 6, a 360 ms segment may include 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal.

At block 106, control circuit 80 determines a metric of signal strength. Determining the metric of signal strength may include determining a maximum signal amplitude during the buffered signal segment associated with the sensed electrophysiological event. For example, control circuit 80 may determine the signal strength metric as the maximum amplitude of the buffered cardiac signal during the signal segment. In one example, control circuit 80 determines the maximum amplitude of the rectified signal segment (or absolute maximum amplitude of a non-rectified signal segment). As described further below, the maximum signal amplitude of each one of multiple buffered signal segments may be determined and the greatest one of the maximum signal amplitudes may be used as a signal strength metric for determining if signal to noise criteria are met at block 110.

At block 108, control circuit 80 determines a metric of the strength or amplitude of possible noise during the buffered signal segment. In one example, control circuit 80 determines the noise strength metric by determining a differential signal from the buffered signal segment. For instance, control circuit 80 may determine a first order differential signal by determining the difference between each pair of consecutive sample points of the notch filtered cardiac electrical signal segment. In other examples, a higher order differential signal may be determined, e.g., second order or higher. Alternatively, the differential signal may be produced by a high pass filter with a sharp corner cut-off frequency, e.g., a cut-off frequency of at least 50 Hz or 60 Hz for example when the sampling frequency is 256 Hz. The maximum absolute amplitude of the differential signal of the buffered signal segment is determined at block 108 as a noise strength metric in one example.

At block 110, control circuit 80 determines if signal to noise criteria are met based on the signal strength metric and the noise strength metric. In some examples, control circuit 80 may determine if signal to noise criteria are met based on the signal strength metric and/or the noise strength metric determined from multiple signal segments, which may be consecutively buffered signal segments. For example the greatest signal strength metric determined from multiple signal segments and the noise strength metric determined from the current signal segment may be compared to signal to noise criteria for determining whether the current signal segment is detected as a noise segment. The number of signal segments that control circuit 80 determines the maximum signal strength metric from may occur over a predetermined time interval expected to include at least one true electrophysiological event e.g., at least one true R-wave, as further described below in conjunction with FIG. 6. The signal to noise criteria may include one or more requirements applied to one or more signal strength metrics and/or one or more noise strength metrics, individually or in one or more combinations, e.g., as one or more ratios of a signal strength metric to a noise strength metric.

In some examples, the signal to noise criteria include a signal strength criterion and a noise strength criterion. The signal strength criterion may be applied to the maximum signal strength metric, e.g., the greatest maximum amplitude determined from one or more preceding, recently buffered signal segments. The maximum signal strength metric is an indication of the amplitude of an expected cardiac event signal that may have occurred during a preceding signal segment. The noise strength criterion may be applied to the noise strength metric of the currently buffered signal segment, e.g., the maximum amplitude of the differential signal of the currently buffered signal segment. In this example, control circuit 80 identifies the greatest maximum amplitude out of recently buffered signal segments as an indication of cardiac event signal strength and identifies the maximum amplitude of the differential signal of the currently buffered signal segment as an indication of the noise strength in the currently buffered signal segment. Control circuit 80 uses these metrics to determine when signal to noise criteria are met at block 110. In other examples, control circuit 80 may determine a ratio of the maximum signal strength metric to the maximum noise strength metric and compare this ratio to a minimum ratio threshold to determine when the signal to noise criteria are met.

Figure 6:
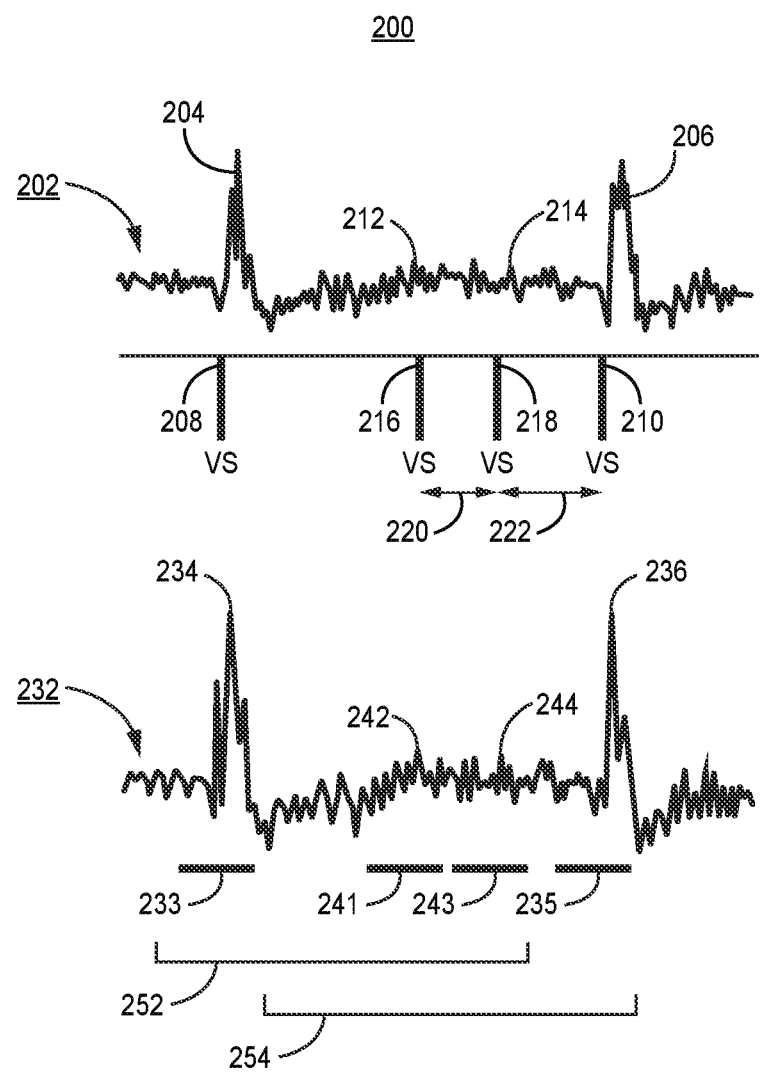
FIG. 6 is diagram of a first cardiac electrical signal and a second cardiac electrical signal illustrating analysis performed by a medical device according to one example for determining if signal to noise criteria are met for increasing the gain of a differential signal for noise detection.

FIG. 6 is a diagram 200 of a first cardiac electrical signal 202 and a second cardiac electrical signal 232 illustrating analysis performed according to one method for determining if signal to noise criteria are met for increasing the gain of the differential signal. In the first cardiac electrical signal 202, two true R-waves 204 and 206 are sensed by the first sensing channel 83 resulting in respective R-wave sensed events signals 208 and 210. However, due to non-cardiac noise present in the first cardiac electrical signal 202, two noise pulses 212 and 214 are each sensed by R-wave detector 66 resulting in false R-wave sensed events signals 216 and 218. Each of the R-wave sensed event signals 208, 210, 216 and 218, denoted by "VS" to indicate a ventricular sensed event, trigger buffering of a segment of the second cardiac electrical signal 232 over a respective time interval 233, 235, 241, and 243.

Each time interval 233, 235, 241, and 243 may extend before and after the time of the respective R-wave sensed event signal 208, 210, 216, and 218 such that the associated buffered second cardiac electrical signal segment includes sample points before and after the time of the associated R-wave sensed event signal. As indicated above, in one example, each time interval 233, 235, 241 and 243 is about 360 ms in duration so that the respective second cardiac electrical signal segment buffered over the time interval includes 92 sample points when the sampling rate is 256 Hz with 24 of the sample points occurring after the R-wave sensed event signal that triggered the storage of the signal segment and 68 sample points extending from the R-wave sensed event signal earlier in time from the R-wave sensed event signal. Each cardiac electrical signal segment corresponding to a respective time interval 233, 235, 241 or 243 encompasses the time of a single one R-wave sensed event signal.

Control circuit 80 determines a maximum absolute amplitude 234 of the buffered cardiac electrical signal segment over time interval 233, maximum absolute amplitude 242 of the buffered cardiac electrical signal segment over time interval 241, and maximum absolute amplitudes 244 and 236 over the cardiac electrical signal segments buffered over respective time intervals 243 and 235. This process of determining maximum amplitudes of each buffered second cardiac electrical signal segment may correspond to determining a metric of R-wave signal strength at block 106 of FIG. 5 described above. These maximum amplitudes 234, 242, 244 and 236 may be stored in a first-in-first-out buffer so that the maximum amplitude of each one of multiple second cardiac electrical signal segments is buffered in a rolling, first-in-first-out buffer. The buffer may store a predetermined number of maximum amplitudes, e.g., 3 to 10 maximum amplitudes corresponding to the most recent 3 to 10 most recent cardiac electrical signal segments and associated R-wave sensed event signals.

In other examples, the maximum amplitude buffer may store each of the maximum amplitudes determined from second cardiac electrical signal segments that are buffered in response to each R-wave sensed event signal during at least a predetermined time interval 252, 254. The predetermined time interval, referred to as a maximum amplitude buffer time interval, may be one to two seconds long in some examples. The maximum amplitude buffer time interval is selected so that at least one true R-wave is expected to occur over the time interval 252 or 254. For example, when the time interval 252, 254 is 1.2 seconds, a true R-wave (e.g., R-wave 234 or R-wave 236) is expected to occur within the 1.2 seconds when the true heart rate is as low as 50 beats per minute. The maximum amplitude buffer time interval may correspond to or be based on a lower pacing rate time interval or an expected resting heart rate of the patient. Each maximum amplitude determined from each cardiac electrical signal segment that is buffered during a 1.2 second, 1.5 second, 2.0 second or other selected time interval may be stored in a maximum amplitude buffer. In this case, the number of maximum amplitudes stored in the maximum amplitude buffer may be variable since a different number of R-wave sensed event signals, and thus a different number of cardiac electrical signal segments, may occur during each fixed, predetermined time interval 252, 254 depending on how many non-cardiac noise pulses are oversensed and the actual ventricular rate. When a ventricular blanking interval is set to 150 ms and a maximum amplitude buffer time interval is set to 1.2 seconds, the maximum possible number of R-wave sensed event signals is eight, resulting in eight corresponding cardiac electrical signal segments and eight maximum amplitudes stored in the maximum amplitude buffer.

In the example shown, a maximum amplitude buffer time interval 252, which may be 1.2 seconds long or other selected time interval, extends from a most recent cardiac electrical signal segment buffered over time interval 243 (or from the associated R-wave sensed event signal 218) and includes any preceding cardiac electrical signal segments (or maximum amplitudes) that have been buffered within the maximum amplitude buffer time interval 252. In other examples, the maximum amplitude buffer in memory 82 is configured to store up to a fixed number of maximum amplitudes, e.g., eight maximum amplitudes, on a first in first out basis, each with a corresponding timestamp. When a maximum amplitude is determined for a given cardiac electrical signal segment, the maximum amplitude may be buffered in memory 82 with a time stamp. The maximum amplitudes stored in the maximum amplitude buffer with a time stamp that occurs within the maximum amplitude buffer time interval 252 from the current maximum amplitude time stamp may be evaluated for identifying a likely R-wave from among the maximum amplitudes.

For each cardiac electrical signal segment, therefore, the maximum amplitudes stored with a time stamp that occurs within the maximum amplitude buffer time interval earlier than the current maximum amplitude (or current buffered signal segment) may be identified. In the example of maximum amplitude buffer time interval 252, the maximum amplitude 244 and the preceding maximum amplitudes 234 and 242 occurring earlier but within the maximum amplitude buffer time interval 252 are evaluated for identifying the maximum amplitude that has the greatest probability of being an R-wave during the maximum amplitude buffer time interval. In other examples, maximum amplitudes may be evaluated over a maximum amplitude buffer time interval starting from a maximum amplitude, R-wave sensed event signal or beginning of a cardiac electrical signal segment and going forward in time rather than backward in time as described here. However this may delay determining whether the current cardiac electrical signal segment meets the signal to noise criteria by the one to two second maximum amplitude buffer time interval, which may result in a later detection of noise than going backward in time from the current maximum amplitude.

The greatest maximum amplitude 234 of the buffered maximum amplitudes during time interval 252 is identified by control circuit 80. This greatest maximum amplitude 234 out of the buffered maximum amplitudes 234, 242 and 244 during the one to two second maximum amplitude buffer time interval 252 is presumably a true R-wave amplitude (corresponding to R-wave 204 in this case) and unlikely to be a relatively lower amplitude non-cardiac noise pulse, e.g., caused by skeletal muscle myopotentials. The two lower maximum amplitudes 242 and 244 may be non-cardiac noise pulses that are oversensed as R-waves. This greatest maximum amplitude 234 out of multiple buffered signal segments may be determined as a signal strength metric by control circuit 80, e.g., at block 106 of FIG. 5. As such, determining the signal strength metric may require determining a maximum signal amplitude from multiple consecutive buffered signal segments.

The next R-wave sensed event signal 210 triggers buffering of the next cardiac electrical signal segment (over time interval 235) and the maximum amplitude 236 during the next cardiac electrical signal segment is buffered in the first-in-first-out maximum amplitude buffer, replacing the oldest maximum amplitude 234. The other maximum amplitudes 242 and 244 occurring during the most recent preceding cardiac electrical signal segments (associated with time intervals 241 and 243 respectively), which are within the fixed predetermined time interval 254, remain in the maximum amplitude buffer. Now, the greatest maximum amplitude stored in the maximum amplitude buffer is the maximum amplitude 236, presumably a true R-wave amplitude (corresponding to R-wave 206) because it is the highest amplitude stored in the maximum amplitude buffer.

In this way, the maximum amplitude of each buffered cardiac electrical signal segment occurring during the moving time interval, as denoted by intervals 252 and 254, is buffered so that a likely true R-wave amplitude can be identified over each time interval 252, 254 as an indication of the R-wave signal strength. The greatest maximum amplitude may be determined from the moving time interval 252, 254 and compared to a signal strength threshold at block 110 of FIG. 5 to determine if a first criterion of the signal to noise criteria is met. In one example, the signal strength threshold is set to a percentage or portion of the ADC range of the sensing channel. In the example of rectified cardiac electrical signal segments being buffered from the second cardiac electrical signal sensed by the second sensing channel 85, the ADC 73 may have a range of 127 ADC units, for example. The greatest maximum amplitude may be compared to 30%, 40%, 50% or other percentage or fraction of the maximum ADC range. In one example, the greatest maximum amplitude is compared to one-third of the ADC range of 127 units or 42 ADC units. When the greatest absolute maximum amplitude is greater than 42 ADC units, the R-wave signal strength may satisfy one criterion of the signal to noise criteria applied at block 110 of FIG. 5. In other examples, the signal strength threshold may be set based on previously confirmed R-wave amplitudes, the mean sample point amplitude over the cardiac electrical signal segment or another time interval, or based on another reference amplitude. The signal strength threshold may be selected such that a signal strength metric that is greater than the signal strength threshold likely corresponds to a relatively high R-wave amplitude or true electrophysiological event being sensed by the medical device.

In addition to determining whether the signal strength criterion is met at block 110, control circuit 80 may determine whether a noise strength criterion is met at block 110 of FIG. 5. In one example, control circuit 80 determines the noise strength metric by determining a first order differential signal of the current cardiac electrical signal segment. Using time interval 252 in FIG. 6 as an example, the first order differential signal of the most recent cardiac electrical signal segment (corresponding to time interval 243) is determined. The maximum amplitude of this differential signal is determined and compared to a noise strength threshold. The noise strength threshold may also be defined as a percentage or fraction of the ADC range. In one example, the maximum amplitude of the differential signal of the most recent cardiac electrical signal segment in the time interval 252 is compared to about 10% (or other percentage) of the ADC range, which is a lower percentage or fraction than the signal threshold applied to the greatest maximum amplitude for determining if a signal strength criterion is met. For instance, when the ADC range is 127 ADC units, the noise strength threshold may be 13 ADC units. When the maximum amplitude of the differential signal of the current segment 243 is less than the noise strength threshold of 13 ADC units, the noise strength criterion of the signal to noise criteria applied at block 110 is met.

In some examples, the lowest maximum amplitude buffered in the first in first out buffer or the maximum amplitude of the currently buffered signal may be assumed to be an oversensed noise signal and used as the noise strength metric. However, without filtering lower frequencies from the buffered signal segment corresponding to the frequency of a true electrophysiological event signal for removing a possible true electrophysiological event signal (e.g., a true R-wave signal) before determining the noise strength metric, the lowest maximum amplitude may be a true event signal. For example, the lowest maximum amplitude may be a low amplitude R-wave or fibrillation wave that should not be presumed to be a noise pulse or rejected as possible noise.

When both the signal strength criterion and the noise strength criterion are met at block 110 of FIG. 5, control circuit 80 determines that the signal to noise criteria are satisfied. Generally, the signal strength criterion is met when a presumed R-wave amplitude of a recent cardiac electrical signal segment is greater than a predetermined portion of the ADC range or other selected signal strength threshold. The noise strength criterion is met when the maximum amplitude of the current differential signal segment is less than a predetermined portion of the ADC range or other selected noise strength threshold. In other examples, control circuit 80 may determine the ratio of the maximum signal strength metric to the current noise strength metric and compare this expected signal to noise ratio to a minimum acceptable signal to noise ratio threshold. When the ratio of the maximum signal strength metric to the current noise strength metric is greater than the minimum ratio threshold, control circuit 80 may determine that the signal to noise criteria are satisfied.

When the signal to noise criteria are satisfied, control circuit 80 increases, e.g., doubles, the gain of the cardiac electrical signal being used for detecting noise at block 112. For example, control circuit 80 may adjust the gain of the differential signal of the current cardiac electrical signal segment 243 at block 112 before determining a noise metric from the differential signal segment at block 114. It is to be understood that the gain increase may be applied to the cardiac electrical signal segment before or after determining the differential signal of the segment. The gain of a high pass filtered signal, first order or higher order differential signal, or any cardiac electrical signal segment being used by control circuit 80 for determining a noise metric may be adjusted at block 112 to increase the amplitude of noise pulses that may be present in the signal. When the signal to noise criteria are not met at block 110, control circuit 80 does not adjust the gain of the signal being used for determining a noise metric and may advance directly to block 114 without changing the signal gain.

Control circuit 80 determines the noise metric at block 114 from the current signal segment for detecting the segment as a noise segment (or not a noise segment). In one example, control circuit 80 may determine a noise pulse count as the noise metric. The noise pulse count may be determined by counting pulses defined by consecutive zero crossings of the differential signal segment as described below in conjunction with FIG. 7. In other examples, control circuit 80 may determine the noise metric by counting the number of "wiggles" or oscillations of the signal over the signal segment, counting the number of inflection points in the signal segment, counting the number of peaks, counting the number of crossings of a threshold, determining an integral or summation of rectified sample point amplitudes over the signal segment, determining an average amplitude over the signal segment, determining the high frequency content of the signal, detecting an episode or time interval of frequencies continuously above a noise frequency threshold, or other metric that is correlated to the number and/or amplitude of noise pulses in the signal segment. In other examples, a noise detector may be included in sensing circuit 86 or control circuit 80 configured to detect noise pulses based on amplitude content and/or frequency content of the signal. For example, a noise detector may detect sustained time intervals (e.g. as low as 100 ms time intervals or less, 100 to 500 ms time intervals, or longer time intervals) of high frequency content correlated to noise corruption in the cardiac electrical signal. After increasing the gain of the signal segment used for detecting noise, a variety of noise detection techniques may be utilized by the medical device for detecting noise pulses from the increased gain signal.

In the next cardiac electrical signal segment over time interval 235, the maximum amplitude of the differential signal is likely to exceed the noise strength threshold due to the presence of the large, true R-wave signal associated with peak amplitude 236. In this case, the maximum amplitude of the current differential signal is greater than the noise strength threshold. Thus, the signal to noise criteria for the time interval 254 are not satisfied because the noise strength criterion is not met. The gain of the differential signal over time interval 235 is left unchanged, and control signal 80 advances to block 114 to determine the noise metric from the differential signal of the cardiac electrical signal segment over time interval 235 without the gain adjustment. Determination of a noise metric at block 114 in accordance with one example is described below in conjunction with FIG. 7.

Control circuit 80 determines when noise criteria are met at block 116 based on the determined noise metric and may classify the current cardiac electrical signal segment as a noise segment at block 118. When the noise criteria are unmet at block 116, the current cardiac electrical signal segment is not classified as a noise segment. The process may return to block 102 to wait for the next sensed event signal to repeat the process for the next electrical signal segment buffered in response to the next sensed event signal.

Figure 7:
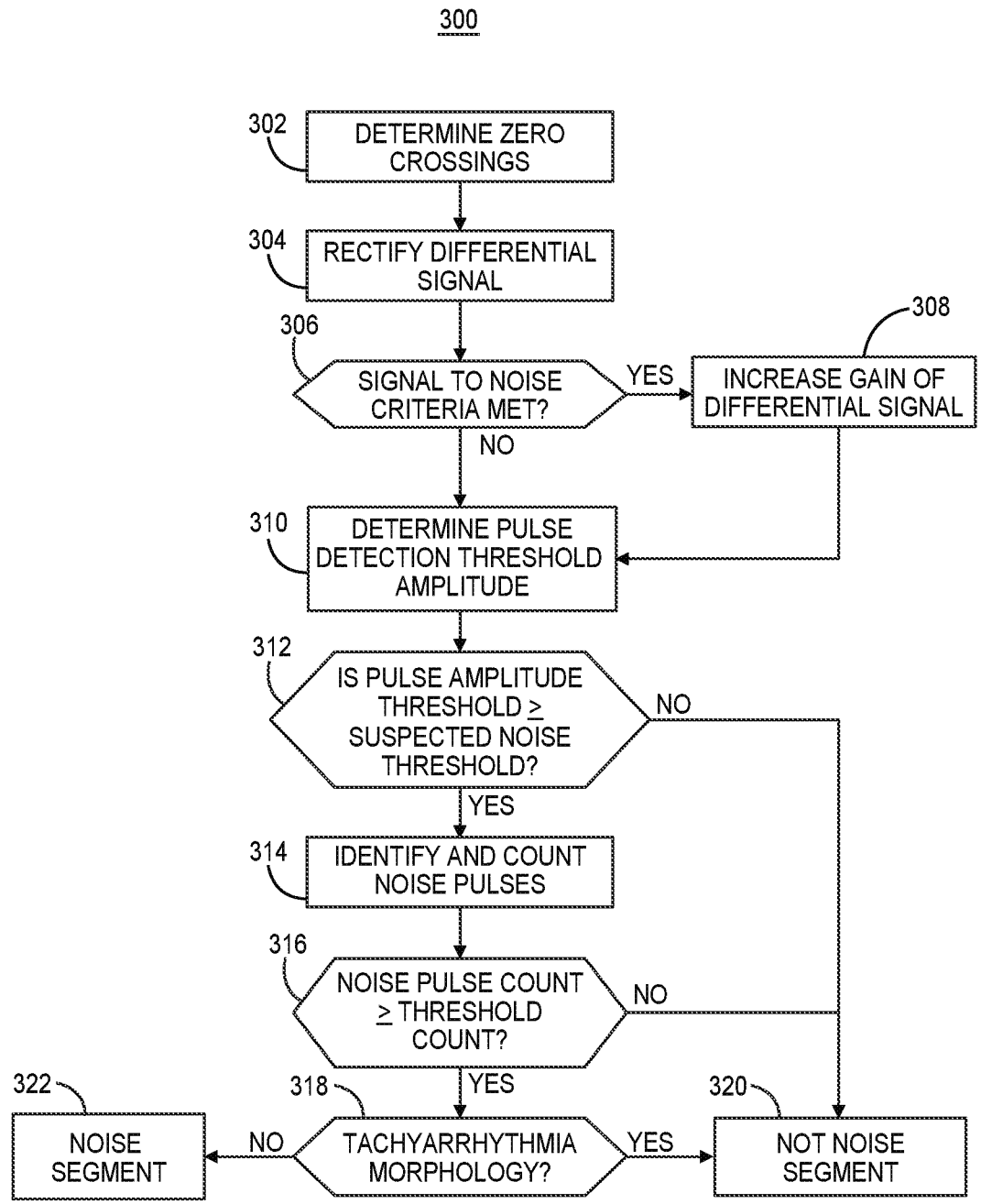
FIG. 7 is a flow chart of a method performed by a medical device for determining a noise metric and classifying a cardiac electrical signal segment as a noise segment or non-noise segment according to some examples.

FIG. 7 is a flow chart 300 of a method for determining a noise metric and classifying a cardiac electrical signal segment as a noise segment or non-noise segment according to some examples. The noise metric may be determined from the first order (or other higher order) differential signal determined from the notch filtered cardiac electrical signal segment buffered from the second sensing channel 85 in some examples. The differential signal is analyzed to determine the noise metric at block 114 of FIG. 5 without changing the gain when the signal to noise criteria are not satisfied at block 110 of FIG. 5 as described above. The noise metric is determined from the differential signal after increasing the gain of the differential signal, e.g., doubling the gain, when the signal to noise criteria are satisfied at block 110 of FIG. 5.

At block 302, control circuit 80 may determine zero crossings of a segment of the differential signal. The differential signal may be received and buffered from second sensing channel 85 as described above or determined by control circuit 80 from the cardiac electrical signal segment buffered from second sensing channel 85. The zero crossings may be determined by identifying a pair of sample points of the differential signal straddling a zero crossing, including one sample point (positive or negative) immediately prior to the zero crossing and a second sample point (negative or positive) immediately after the zero crossing. One sample point of this pair of sample points having the smallest absolute value is identified and set to a zero amplitude by control circuit 80 to demarcate the zero crossing and define the ending point of one signal pulse and starting point of the next consecutive signal pulse. In some instances one of the sample points of the pair of sample points at a zero crossing may have a zero amplitude, and the second sample point may be positive or negative. The zero amplitude sample point may be selected as the zero crossing defining the ending point of one signal pulse and the starting point of the next signal pulse. The zeroed sample points separate and define consecutive pulses of the differential signal as illustrated in FIG. 8.

Figure 8:
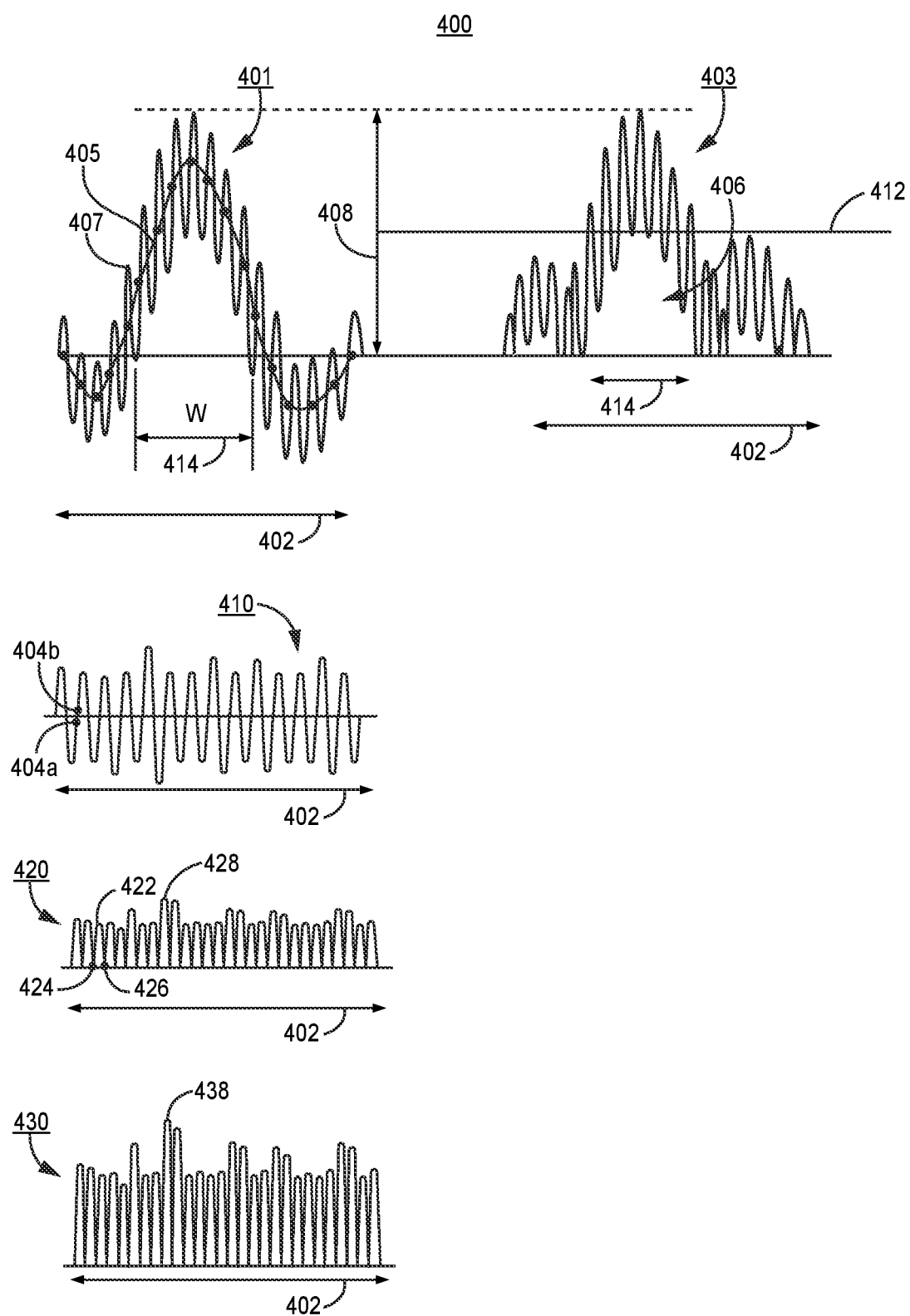
FIG. 8 is a graphical representation of a cardiac electrical signal segment and corresponding first order differential signal.

FIG. 8 is a graphical representation 400 of a cardiac electrical signal segment 401 and corresponding first order differential signal 410. Cardiac electrical signal segment 401 is buffered over time segment 402 in response to an R-wave sensed event signal as generally described above in conjunction with FIG. 6. The R-wave sensed event signal may be associated with a true R-wave or an oversensed noise signal. The first order differential signal 410 of the cardiac electrical signal segment 401 is determined by hardware, firmware and/or software included in sensing circuit 86 and/or control circuit 80 for analysis for detecting noise contamination. A pair of sample points 404a and 404b includes the last sample point 404a before a zero crossing of the first order differential signal 410 and the earliest sample point 404b after the zero crossing. The absolute values of the sample points 404a and 404b are compared by control circuit 80, and the smallest absolute value sample point is set to zero amplitude at block 302 of FIG. 7 to demarcate consecutive pulses of the differential signal 410.

With continued reference to FIGS. 7 and 8, the differential signal is rectified at block 304 of FIG. 7 to produce the rectified differential signal 420 shown in FIG. 8. Each pulse of rectified differential signal 420, for example pulse 422, is defined by two consecutive zeroed sample points 424 and 426. Zeroed sample point 424, for example, may be the smallest absolute amplitude sample point 404a or 404b set to a value of zero to mark the end of the preceding pulse and the onset of pulse 422.

Control circuit 80 determines whether the signal to noise criteria are met at block 306, e.g., according to the techniques described in conjunction with FIGS. 5 and 6. The gain of rectified differential signal 420 is increased at block 308, e.g., doubled or increased by another selected factor, to produce an increased gain signal, e.g., increased gain signal 430 of FIG. 8 when the signal to noise criteria are met.

When the signal to noise criteria are not met, the rectified differential signal 420 without a gain adjustment is analyzed for detecting a noise segment. The process of flow chart 300 advances from block 306 to block 310 without increasing the gain of the rectified differential signal at block 308 before performing noise analysis. It is noted that the gain of differential signal 420 is increased to increase the amplitude of non-cardiac noise pulses to facilitate counting of noise pulses and detection of noise corruption. The gain of the cardiac electrical signal is not increased at block 308 to facilitate R-wave sensing. R-wave sensing from the selected cardiac electrical signal is performed separately and independently of gain adjustments applied to differential signal 420 for noise detection. The R-wave may be sensed from a cardiac electrical signal before the determination that signal to noise criteria are met and before making a gain adjustment to the differential signal.

At block 310, control circuit 80 determines a pulse detection threshold amplitude. The pulse detection threshold amplitude may be determined based on a maximum amplitude of whichever of the rectified differential signal 420 or increased gain signal 430 is being analyzed for noise detection based on the signal to noise criteria. For example, the maximum peak amplitude 428 of rectified differential signal 420 (when signal to noise criteria are unmet) or maximum peak amplitude 438 of increased gain signal 430 (when signal to noise criteria are met) may be determined by determining the maximum amplitude of the respective differential signal 428 or 438 over the time segment 402. The pulse detection threshold amplitude may be set to a fraction or percentage of the greatest maximum amplitude (428 or 438), e.g., one half (or other fraction) of the greatest maximum amplitude. In one example, the pulse detection threshold amplitude is set to one-eighth of the greatest maximum amplitude of the rectified first order differential signal (420 or 430).

At block 312 of FIG. 7, the pulse detection threshold amplitude is compared to a suspected noise threshold amplitude. When the pulse detection threshold amplitude, a fraction or percentage of the maximum amplitude of the differential signal segment, is less than a suspected noise threshold, control circuit 80 may classify the segment as a non-noise segment at block 320. In other examples, the maximum amplitude of the differential signal segment may be compared directly to a suspected noise threshold amplitude. The current cardiac electrical signal segment is determined to not be noise contaminated at block 320 when the pulse detection threshold amplitude is less than a suspected noise threshold. The suspected noise threshold may be set to a value of 1 ADC unit in some examples but may be set to a value of 5 ADC units or less or another selected threshold in various examples.

Referring again to FIG. 8, the noise in cardiac electrical signal segment 401, observed as the noise pulses in the rectified differential signal 420 without increased gain, may go undetected when the maximum pulse amplitude 428 is less than a threshold amplitude (or the pulse detection threshold amplitude set to a portion of the maximum amplitude 428 is less than the suspected noise threshold). However, by increasing the gain of the differential signal 420 to produce the increased gain signal 430, the pulse detection threshold amplitude set based on the increased (e.g., doubled) maximum pulse amplitude 438 may meet or exceed the suspected noise threshold. This enables the control circuit 80 to determine that the cardiac electrical signal segment 401 is suspected to contain noise and enable analysis of the increased gain signal 430 to determine if the corresponding signal segment 401 is noise corrupted.

When low amplitude myopotential noise is present in the signal segment, for example as represented by the signal pulses of signal segment 401 and the first order differential signal 410, oversensing of myopotential noise may cause a VT or VF NID to be reached. When this myopotential noise is not identified or detected, a false VT or VF detection may be made leading to therapy delivery. By increasing the gain of the first order differential signal when the signal to noise criteria are met, the myopotential noise pulses are more readily detectable, enabling a noise-contaminated signal segment to be identified thereby avoiding a false VT or VF detection and unnecessary VT or VF therapy.

Referring again to FIG. 7, when the pulse detection threshold amplitude is greater than or equal to the suspected noise threshold at block 312, control circuit 80 identifies and counts noise pulses present in the differential signal segment to determine if the segment is noisy. Each pulse of the rectified differential signal 420 (when the signal to noise criteria are not met) or the increased gain rectified, differential signal 430 (when the signal to noise criteria are met), defined by the sample points between two consecutive zeros, may be counted. In some examples, control circuit 80 may count a pulse as a noise pulse only when the pulse meets noise pulse criteria at block 314.

The noise pulse criteria may include pulse amplitude criteria and/or pulse width criteria. For instance, a pulse may be counted as a noise pulse at block 314 when the pulse has an amplitude greater than the pulse detection threshold amplitude and a pulse width, defined by the number of sample points between the consecutive zeros defining the pulse, that is less than or equal to a pulse width threshold. The pulse width threshold may be set to a sample point number of six or less but may be set to other values depending in part on the sampling rate. When the maximum amplitude between consecutive zeros is less than or equal to the pulse detection threshold amplitude and/or the number of sample points between consecutive zeros is greater than the pulse detection threshold width, the pulse is not counted as a noise pulse at block 314.

At block 316, control circuit 80 compares the number of pulses meeting noise pulse criteria and thus counted as noise pulses at block 314 to a threshold count. When the number of noise pulses counted is less than the threshold count, the cardiac electrical signal segment from which the differential signal was derived is classified as a non-noise segment at block 320. The current cardiac electrical signal segment is determined to not be noise contaminated. The associated R-wave sensed event signal is presumed to be a true sensed R-wave or at least not a non-cardiac noise signal. This determination based on the second cardiac electrical signal may be extended to the first cardiac electrical signal such that both signals are determined to be clean signals, without non-cardiac noise contamination, when the noise pulse count determined from one cardiac electrical signal is less than the noise threshold count. When the number of noise pulses counted equals or exceeds the threshold count, however, the cardiac electrical signal segment may be classified as a noise segment at block 322. This classification may be extended to the first cardiac electrical signal such that the R-wave sensed event signal that triggered the buffering of the second cardiac electrical signal may be a falsely sensed R-wave due to non-cardiac noise.

In some examples, before classifying the cardiac electrical signal segment as a noise segment at block 322, control circuit 80 may determine if a tachyarrhythmia morphology is present in the cardiac electrical signal segment at block 318. The presence of a tachyarrhythmia morphology may preclude classification of a signal segment as a noise segment to avoid withholding a tachyarrhythmia detection due to noise detection when evidence of tachyarrhythmia morphology is detected in the cardiac electrical signal segment. Evidence of tachyarrhythmia morphology may be detected at block 318 based on a gross morphology analysis of the signal segment. Instead of counting individual pulses in the differential signal segment, the gross morphology of the cardiac electrical signal segment, e.g., signal segment 401, may be analyzed to assess the morphology of the overall waveform 405 that the noise pulses 407 may be riding one. For instance, control circuit 80 may determine a signal amplitude metric and signal width metric of the overall signal segment, e.g., using rectified signal segment 403 in FIG. 8. Methods for determining a gross morphology signal amplitude metric and a gross morphology signal width metric for detecting evidence of a tachyarrhythmia morphology at block 318 of FIG. 7 are described below in conjunction with FIGS. 8-10. A gross morphology signal amplitude and signal width that is correlated to a sinusoidal-like fibrillation waveform may be detected as evidence of a tachyarrhythmia morphology, for example.

Control circuit 80 may classify the cardiac electrical signal segment as a non-noise segment at block 320 when a tachyarrhythmia morphology is determined to be present ("yes" branch of block 318), even though the noise pulse count may meet the threshold count for detecting non-cardiac noise at block 316. When a tachyarrhythmia morphology is not detected at block 318 ("no" branch), the cardiac electrical signal segment is detected as a noise segment at block 322 in response to the noise pulse count meeting the threshold count at block 316.

Figure 9:
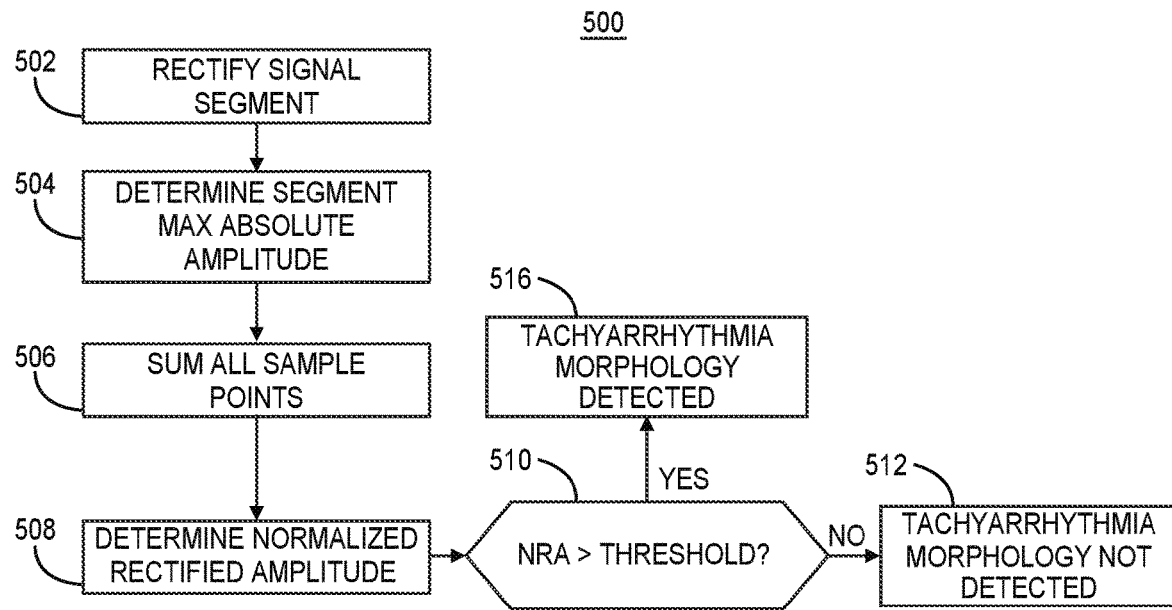
FIG. 9 is a flow chart of a method for determining a gross morphology amplitude metric of a cardiac electrical signal segment for detecting a tachyarrhythmia morphology according to one example.

FIG. 9 is a flow chart 500 of a method for determining a gross morphology amplitude metric of a cardiac electrical signal segment for detecting a tachyarrhythmia morphology according to one example. Each cardiac electrical signal segment analyzed for determining a gross morphology metric may be buffered as generally described above in conjunction with FIG. 6. The method of flow chart 500 may generally be performed at block 318 of FIG. 7 to analyze a cardiac electrical signal segment, which may be suspected of being a noise contaminated signal.

At block 502, the second cardiac electrical signal segment stored on a triggered basis in response to an R-wave sensed event signal may be rectified. In some examples, a 360 ms segment of the notch-filtered second cardiac electrical signal may be rectified by rectifier 75 included second sensing channel 85. At block 502, the buffered, rectified signal segment may be retrieved by control circuit 80 from memory 82. In other examples, a notch-filtered signal segment may be buffered in memory 82, and control circuit 80 may perform the rectification of the stored signal segment at block 502. A rectified signal segment 403 buffered over time segment 402 is shown in FIG. 8. The rectified signal segment, e.g., segment 403, obtained at block 502 may correspond to a signal segment identified as a suspected noise segment based on the maximum amplitude of the differential signal and the differential signal noise pulse count as described in conjunction with FIG. 7.

With continued reference to FIGS. 8 and 9, control circuit 80 determines the maximum absolute amplitude 408 of the rectified, notch-filtered signal segment 403 at block 504. The maximum absolute amplitude 408 may be determined from among all sample points spanning the selected signal segment 403. As described above, a 360 ms segment of the second cardiac electrical signal may include 92 sample points when the sampling rate is 256 Hz, with 24 of the sample points occurring after the R-wave sensed event signal that triggered the storage of the signal segment and 68 sample points extending from the R-wave sensed event signal earlier in time from the R-wave sensed event signal.

At block 506, the amplitudes of all sample points of the rectified signal segment are summed, which represents the area 406 of the rectified signal segment 403. At block 508, a gross morphology amplitude metric of the signal segment is determined as a normalized rectified amplitude (NRA) based on the maximum absolute amplitude 408 determined at block 504 and the summed sample point amplitudes (area 406) determined at block 506. In one example, the NRA is determined as a predetermined multiple or weighting of the summation of all sample point amplitudes of the notch-filtered and rectified signal segment 403 normalized by the maximum amplitude 408. For instance, the NRA may be determined as four times the summed amplitudes (area 406) divided by the maximum absolute amplitude 408, which may be truncated to an integer value. This NRA may be determined as a gross morphology amplitude metric at block 318 of FIG. 7 for detecting a tachyarrhythmia morphology based on the sample points spanning the signal segment that extends before and after the R-wave sensed event signal. As can be seen in the illustrations of FIG. 8, the gross morphology amplitude metric determined from the maximum amplitude 408 and area 406 represents an amplitude metric of the underlying cardiac signal waveform 405 that the individual non-cardiac noise pulses 407 may be riding on. As such, the noise pulse count described in conjunction with FIG. 7 is useful in detecting non-cardiac noise pulses 407 that may be contaminating the overall cardiac signal waveform 405 whereas the gross morphology amplitude metric, and the gross morphology width metric described below, are useful in detecting a gross morphology of the underlying cardiac signal waveform 405 in the signal segment 403 that may correspond to a tachyarrhythmia waveform morphology.

For example, the gross morphology amplitude metric determined as the weighted area 406 divided by the maximum amplitude 408 may be inversely correlated to the probability of the signal segment sample points being at a baseline amplitude during the time segment 402. The higher the gross morphology amplitude metric is, the lower the probability that the signal is at a baseline amplitude at any given time point during the time segment 402. A relatively low probability that the signal 403 is at baseline during the time segment 402 may be correlated to a tachyarrhythmia morphology, e.g., a ventricular fibrillation morphology, which may resemble a sinusoidal signal. When the gross morphology amplitude metric exceeds a threshold value the more likely the cardiac electrical signal segment has a tachyarrhythmia morphology. When the gross morphology amplitude metric is less than the threshold value, the higher the probability that the signal is at a baseline amplitude at a given time point during the time segment 402 of the signal segment 403. A relatively higher probability of a signal sample point being at baseline during the time segment 402 may be correlated to a relatively narrow R-wave signal occurring during the signal segment, or no true R-wave being present, with baseline amplitude portions of the signal segment occurring before and after the R-wave sensed event signal. As such, when a tachyarrhythmia morphology is not detected and the noise pulse count reaches a threshold count value, as described above, the R-wave sensed event signal associated with the cardiac electrical signal segment may correspond to a non-cardiac noise pulse rather than a true R-wave.

When the gross morphology amplitude metric is greater than a predetermined threshold, "yes" branch of block 510, evidence of an underlying large amplitude cardiac signal that may correspond to a tachyarrhythmia morphology is detected at block 516. In this case, detection of the tachyarrhythmia morphology precludes detecting the signal segment as a noise segment as described above in conjunction with FIG. 7. When the NRA is less than or equal to the NRA threshold ("no" branch of block 510), a tachyarrhythmia morphology is not detected at block 512. The segment may be detected as a noise segment, depending on the analysis of the pulse count described above in conjunction with FIG. 7. The NRA threshold for detecting a tachyarrhythmia morphology applied at block 510 may be set between 100 and 150, and is set to 125 in some examples, such as when 92 sample points are summed and multiplied by a weighting factor of four and normalized by the maximum absolute amplitude. The NRA threshold to detect a tachyarrhythmia morphology in the cardiac electrical signal segment may depend on various factors such as the amplification and number of sample points summed, the multiplication or weighting factor of the summed sample points, etc.

Figure 10:
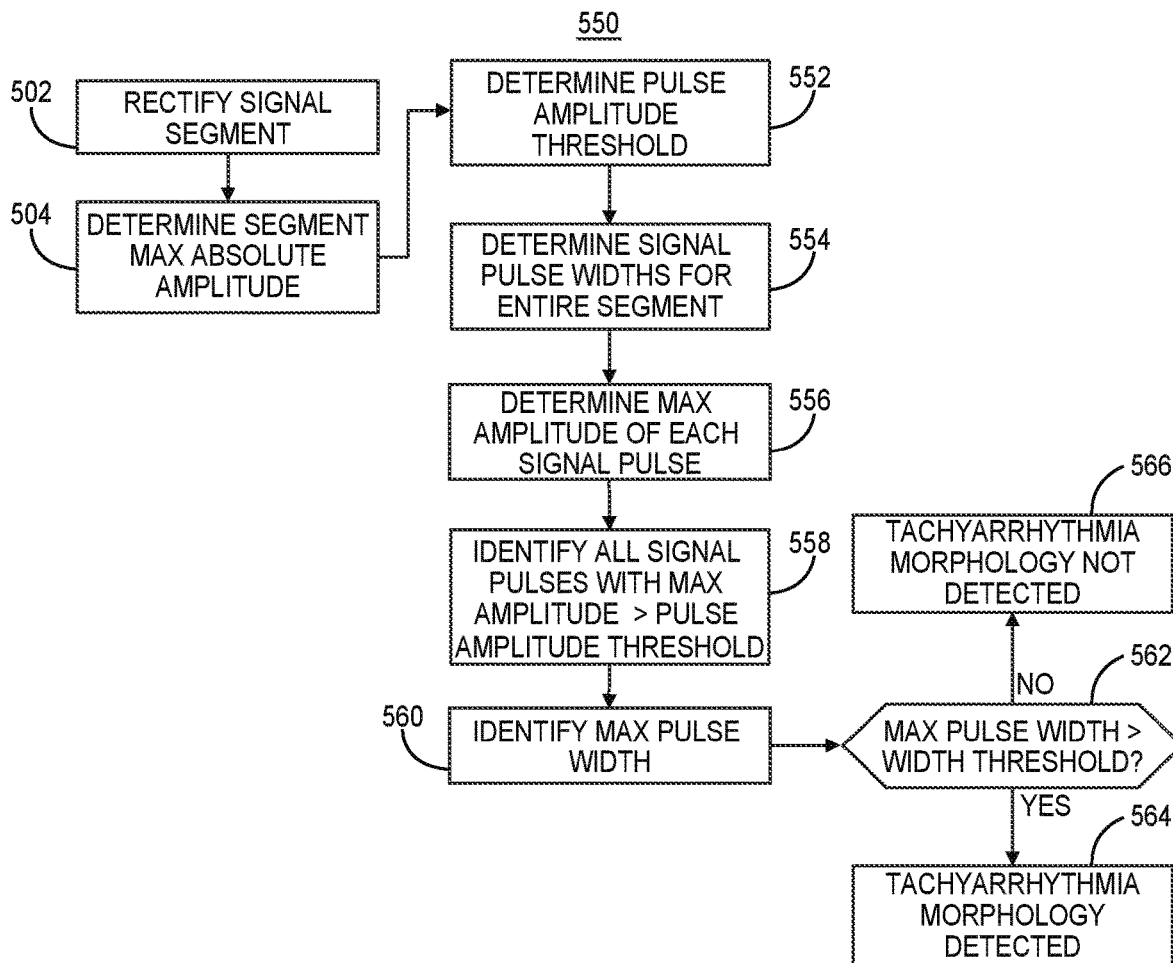
FIG. 10 is a flow chart of a method for detecting a tachyarrhythmia morphology in a cardiac electrical signal segment based on a gross morphology signal width metric according to one example.

FIG. 10 is a flow chart 550 of a method for detecting a tachyarrhythmia morphology in a cardiac electrical signal segment based on a gross morphology signal width metric according to one example. The process of flow chart 550 may be performed by control circuit 80 for determining a gross morphology signal width metric at block 318 of FIG. 7. Blocks 502 and 504 correspond to identically-numbered blocks described above in conjunction with FIG. 9. The notch-filtered, rectified cardiac electrical signal segment, e.g., signal segment 403 shown in FIG. 8, determined at block 502 may be used to determine the maximum absolute amplitude 408 of the signal segment 403 at block 504.

With continued reference to FIGS. 8 and 10, control circuit 80 determines a pulse amplitude threshold 412 at block 552 based on the maximum absolute amplitude 408 determined at block 504. This pulse amplitude threshold 412 may be used for identifying a signal pulse having a maximum signal width out of all signal pulses occurring during the time segment 402 of the cardiac electrical signal segment 403. For example, the pulse amplitude threshold 412 used for determining the gross morphology signal width metric may be set to half the maximum absolute amplitude 408 of the rectified, notch-filtered signal segment 403.

At block 554, control circuit 80 determines the signal width for all signal pulses of the second cardiac electrical signal segment 403. Each signal pulse in the signal segment 403 may be identified by identifying two consecutive zero amplitude or baseline amplitude sample points of the rectified signal segment 403. All signal pulses between two consecutive baseline amplitude sample points are identified. The signal pulses may be identified from the non-rectified signal segment 401 to enable signal pulses to be identified between zero-crossings, in some examples. The signal width of each identified signal pulse is determined as the number of sample points (or corresponding time interval) between the pair of consecutive baseline amplitude sample points (or zero crossings). The absolute maximum amplitude of each rectified signal pulse is determined at block 556. All signal pulses of the rectified signal segment 403 that have an absolute maximum amplitude that is greater than or equal to the pulse amplitude threshold 412 are identified at block 558. For example, all signal pulses having a maximum amplitude that is at least half the maximum absolute amplitude 408 determined at block 504 are identified at block 558. Control circuit 80 determines the maximum signal pulse width at block 560 of all identified signal pulses. The number of sample points spanning each identified signal pulse are counted and compared to determine the maximum signal pulse width out of all signal pulses identified at block 558 as having an amplitude that is at least the pulse amplitude threshold 412. The maximum pulse width, e.g., pulse width 414 in FIG. 8, is identified at block 560 and is determined as the gross morphology signal width metric for detecting a tachyarrhythmia morphology (e.g., at block 318 of FIG. 7). This maximum signal pulse width 414 is expected to be the pulse width of the underlying cardiac signal waveform 405.

This gross morphology signal width metric may be correlated to the probability of the signal segment 401 having a tachyarrhythmia morphology. For example, a relatively high gross morphology signal width metric may be evidence of a tachyarrhythmia morphology, such as a relatively wide ventricular fibrillation wave. Conversely, a relatively low gross morphology signal width metric may be evidence of a relatively narrow, true R-wave occurring during the time segment 402 of the cardiac electrical signal segment 401 or absence of a true cardiac signal. When a relatively wide signal pulse is not detected from the rectified cardiac electrical signal segment 403, an oversensed non-cardiac noise pulse may be present and may have triggered the buffering of the cardiac signal segment 401.

Control circuit 80 compares the maximum pulse width 414 identified at block 560 to a pulse width threshold at block 562. In one example, the pulse width threshold is set to 20 sample points when the sampling rate is 256 Hz. When the maximum signal pulse width is less or equal to the width threshold, control circuit 80 does not detect a tachyarrhythmia morphology at block 564. A maximum signal pulse width that is less than or equal to the width threshold may correspond to a true, relatively narrow R-wave, e.g., during a sinus rhythm or to a non-cardiac noise pulse. Control circuit 80 may detect a noise segment at block 322 of FIG. 7 when the maximum signal pulse width is less than or equal to the width threshold (tachyarrhythmia morphology not detected at block 318) and at least a threshold number of pulses are counted from the differential signal (block 316 of FIG. 7).

When the maximum pulse width is greater than the width threshold at block 562, the relatively wide maximum signal pulse width may be detected as evidence of a tachyarrhythmia waveform morphology at block 564. Evidence of the tachyarrhythmia morphology in signal segment 401 precludes detection of a noise segment, even when a threshold number of noise pulses are counted from the differential signal 410 derived from the cardiac electrical signal segment 401. When the tachyarrhythmia morphology is detected based on the gross morphology signal width metric, the signal segment may not be detected as a noise segment.

In some cases, e.g., when only noise pulses are present in the cardiac electrical signal segment, no signal pulses having a maximum amplitude greater than the pulse amplitude threshold may be identified at block 558 of FIG. 10. In this case, the gross morphology width metric is not determined, and a tachyarrhythmia morphology is not detected. The cardiac electrical signal segment may be detected as a noise segment based on the noise pulse count.

In various examples, both the gross morphology amplitude metric and the gross morphology signal width metric may be determined (at block 318 of FIG. 7 according to the techniques of FIG. 9 and FIG. 10, respectively) and compared to respective tachyarrhythmia morphology thresholds. In some examples, both of the gross morphology amplitude metric and the gross morphology signal width metric may be required to be less than or equal to the respective tachyarrhythmia morphology threshold for the tachyarrhythmia morphology to not be detected, enabling a noise segment to be detected. When either one of the gross morphology amplitude or the gross morphology signal width is greater than the respective tachyarrhythmia morphology threshold value, evidence of a tachyarrhythmia morphology may be detected in the cardiac electrical signal segment at block 318 of FIG. 7, precluding detection of a noise segment. In other examples, both of the gross morphology amplitude and signal width metric may be required to be greater than the respective tachyarrhythmia morphology threshold value in order to detect a tachyarrhythmia morphology and preclude detection of a noise segment. If one of the gross morphology metrics, e.g., the amplitude or width metric, is less than or equal to the respective tachyarrhythmia morphology threshold, the tachyarrhythmia morphology criteria may not be met at block 318, allowing the signal segment to be detected as a noise segment at block 322.

The gross morphology amplitude metric determined by the method of FIG. 9 and the gross morphology signal width metric determined by the method of FIG. 10 may be used in combination to detect evidence of a tachyarrhythmia morphology at block 318 of FIG. 7 to prevent detection of a noise segment as described above. A segment of the cardiac electrical signal that has a relatively high gross morphology amplitude metric and/or relatively high gross morphology signal width metric is evidence of a tachyarrhythmia morphology and is not counted as a noise segment that may lead to withholding of a tachyarrhythmia detection and subsequent therapy to maintain a high sensitivity to tachyarrhythmia detection.

Figure 11:
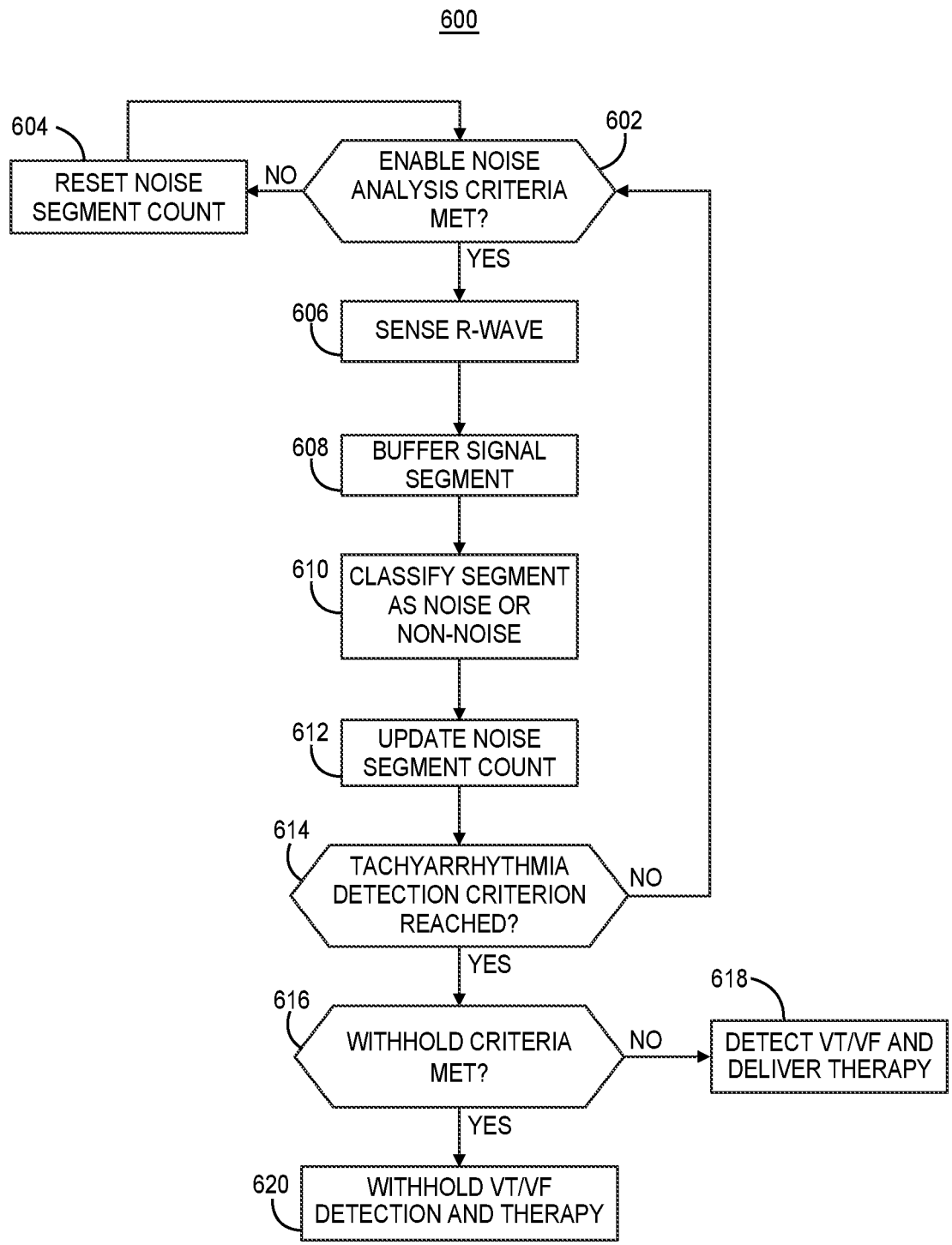
FIG. 11 is a flow chart of a method for controlling tachyarrhythmia detection and therapy delivery by a medical device performing the noise detections disclosed herein according to one example.

FIG. 11 is a flow chart 600 of a method for controlling tachyarrhythmia detection and therapy by a medical device according to one example. At block 602, control circuit 80 of ICD 14 may determine if criteria for enabling signal analysis for detecting noise segments are met. In one example, the criteria for enabling analysis for noise detection requires a threshold number of tachyarrhythmia intervals. For instance, a threshold number of VT and/or VF intervals less than the NID required to detect VT or VF may trigger signal analysis for detection of noise contaminated signal segments. For instance, three, five, eight or other selected number of RRIs falling into the VT and/or VF interval zones may be required to enable signal analysis for noise detection at block 602.

In other examples, noise analysis criteria may be met when a patient activity signal indicates that the patient is engaged in physical activity. For example, a patient activity metric may be determined from an accelerometer included in ICD 14 or another physiological sensor signal. When the patient activity metric indicates that the patient is engaged in physical activity above a resting or predetermined threshold level, the noise analysis may be enabled at block 602.

In still other examples, a threshold change in heart rate based on R-wave sensed event signals may meet noise analysis criteria at block 602. An increase in heart rate, e.g., based on RRIs less than a predetermined threshold interval, a threshold decrease in a median RRI or other heart rate metric, may be an indication that noise pulses are being oversensed. As such, in some cases criteria for enabling noise analysis based on heart rate may not require RRIs falling into a tachyarrhythmia interval zone. An increase in heart rate that occurs quickly or a heart rate above a sub-tachyarrhythmia threshold rate may cause noise analysis criteria to be met at block 602.

The noise analysis criteria may require a combination of two or more criteria in some examples. For instance, a threshold heart rate or tachyarrhythmia interval count and a threshold patient activity level may be required in order to enable noise analysis at block 602. When the criteria for enabling signal analysis for noise detection are met at block 602, control circuit 80 waits for the next R-wave sensed event signal from sensing circuit 86 at block 606 and buffers a corresponding cardiac electrical signal segment at block 608. In some examples, the cardiac electrical signal segment is buffered from the second cardiac electrical signal from second sensing channel 85 when the R-wave is sensed by the first sensing channel 83 from the first cardiac electrical signal. In other examples, the cardiac electrical signal segment may be buffered from the same cardiac electrical signal from which the R-wave was sensed.

At block 610, control circuit 80 performs the noise analysis to classify the cardiac electrical signal segment as a noise segment or not a noise segment. Control circuit 80 may classify the cardiac electrical signal segment as noise or non-noise according to any of the example techniques described above in conjunction with FIGS. 5-10. In general, a noise metric such as a noise pulse count, inflection count, integral or summation of sample point amplitudes, high frequency content or other noise metric correlated to the number, frequency and/or amplitude of noise pulses may be determined from the differential signal of the cardiac electrical signal. The noise metric may be determined after increasing the gain of the differential signal when signal to noise criteria are met as described above. When the noise metric exceeds a noise threshold value, the segment may be classified as a noise segment. When a tachyarrhythmia morphology is detected, e.g., according to the techniques described in conjunction with FIGS. 8-10, the segment may be classified as a non-noise segment, such that the noise segment classification is withheld when the noise metric exceeds the noise segment threshold but a tachyarrhythmia morphology is detected.

Control circuit 80 updates a noise segment count at block 612. A first-in-first-out buffer in memory 82 may set a flag indicating the classification of each cardiac electrical signal segment analyzed. The buffer may store a flag value (e.g., 1=noise segment and 0=non-noise segment) for each of a predetermined number of cardiac electrical signal segments. For example, the buffer may store the classification of each of six, eight, ten, twelve or other selected number of consecutive cardiac electrical signal segments analyzed on a first-in-first-out basis. An X of Y counter may be implemented in control circuit 80 that is updated with each new signal segment classification.

At block 614, control circuit 80 may determine when one or more tachyarrhythmia detection criterion are met. In some examples, tachyarrhythmia detection criteria applied at block 610 may include an interval-based criterion, such as a required NID being reached by the VT interval counter, VF interval counter, or a combined VT/VF interval counter of tachyarrhythmia detection circuit 92. In other examples, the tachyarrhythmia detection criteria determined to be met or unmet at block 610 may be based on QRS waveform morphology meeting morphology-based criteria or a combination of interval or rate-based criteria and morphology-based criteria.

When no tachyarrhythmia detection criteria are met at block 614, control circuit 80 may return to block 602 to continue performing the signal analysis for noise detection as long as the criteria for enabling noise detection remains satisfied at block 602. When the criteria for enabling signal analysis for noise detection becomes unmet (e.g., patient activity, heart rate, and/or the VT and/or VF interval count falls below a respective threshold for enabling noise detection), the count of the noise segments may be cleared at block 604. For example, a buffer storing classifications of signal segments as noise or non-noise segments may be cleared or reset to all non-noise segment values at block 604.

When at least one criterion for detecting tachyarrhythmia is determined to be satisfied at block 614, control circuit 80 may compare the current noise segment count to withhold criteria at block 616. For example, when the number of noise segments counted reaches or exceeds a withhold threshold, the withhold criteria may be met, and the tachyarrhythmia detection based on at least one satisfied tachyarrhythmia detection criterion is withheld by control circuit 80 at block 620. VT or VF is not detected by control circuit 80 at block 620 when the NID is reached, for example, and a threshold number of cardiac electrical signal segments have been classified as noise segments. In some examples, a single noise segment may meet withhold criteria. When control circuit 80 detects a noise segment, the associated sensed R-wave may be rejected, resulting in the NID not being reached.

A tachyarrhythmia therapy that is programmed to be delivered in response to the VT or VF detection is not scheduled or delivered. In other examples, the VT or VF detection may be made in response to tachyarrhythmia detection criteria being satisfied at block 614, but the therapy may be withheld when the number of noise segments meets or exceeds the withhold criteria. When the withhold criteria are not met at block 616, e.g., when the noise segment count is less than a withhold threshold, the tachyarrhythmia is detected at block 618 by control circuit 80 based on the tachyarrhythmia detection criterion being met. Therapy, e.g., ATP and/or CV/DF shock, may be delivered in response to the tachyarrhythmia detection.

Figure 12:
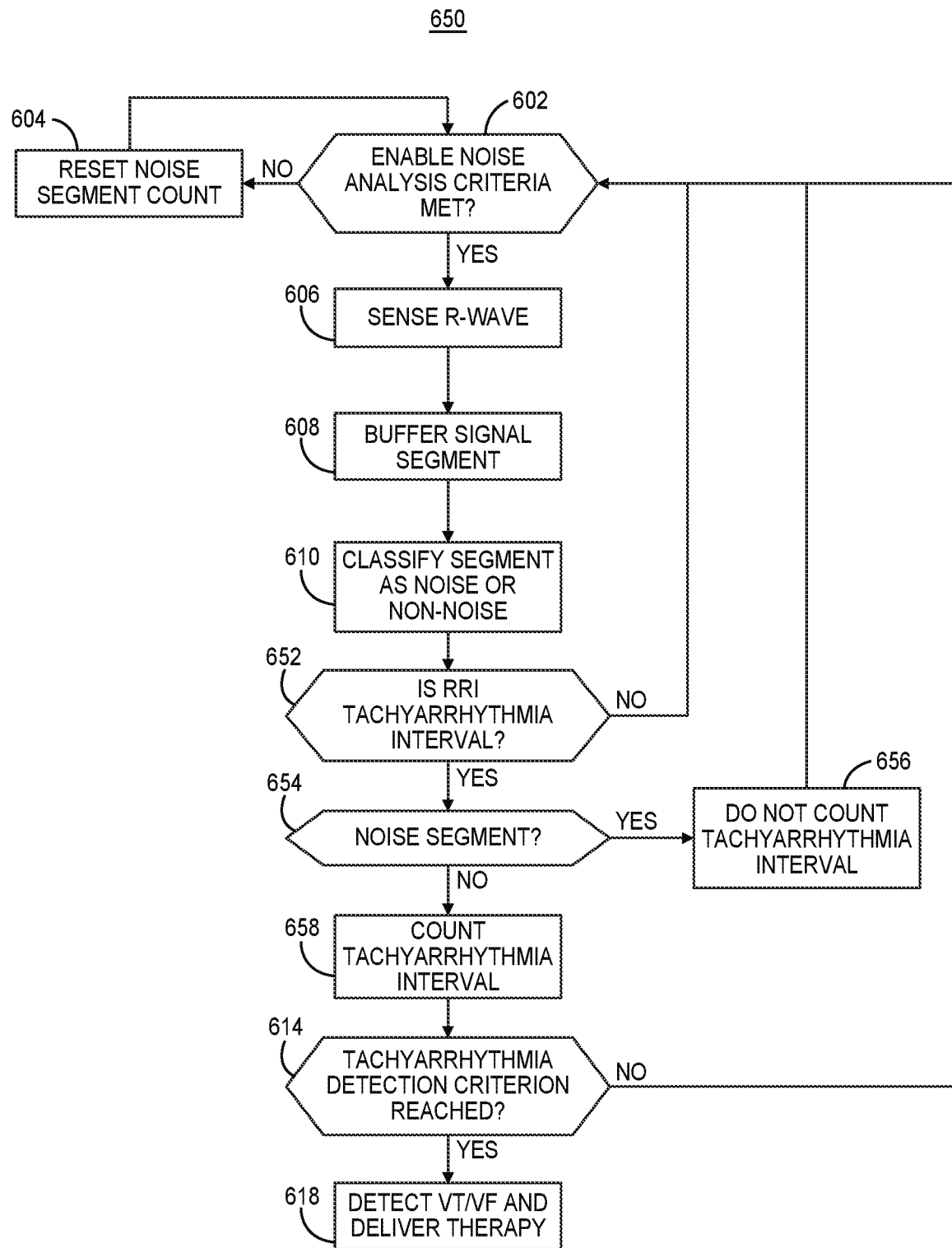
FIG. 12 is a flow chart of an alternative method for controlling tachyarrhythmia detection and therapy by a medical device.

FIG. 12 is a flow chart 650 of an alternative method for controlling tachyarrhythmia detection and therapy by a medical device. In FIG. 12, identically numbered blocks correspond to functions described above in conjunction with FIG. 11 for like-numbered blocks. In the process of FIG. 12, control circuit 80 classifies each cardiac electrical signal segment as noise or non-noise at block 610 when the noise analysis criteria are met at block 602.

After classifying the cardiac electrical signal segment at block 610, control circuit 80 may be configured to ignore the R-wave sensed event signal associated with the cardiac electrical signal segment. When the segment is classified as a noise segment, control circuit 80 may ignore the R-wave sensed event signal without determining an RRI in some examples. In the example shown in FIG. 12, control circuit may determine if the RRI ending with the R-wave sensed event signal associated with the current cardiac electrical signal segment is a tachyarrhythmia interval at block 652.

If so, control circuit 80 determines if the current cardiac electrical signal segment is classified as a noise segment at block 654. If the signal segment associated with the R-wave sensed event signal ending a tachyarrhythmia is classified as a noise segment ("yes" branch of block 654), control circuit 80 does not count the tachyarrhythmia interval as a VT or VF interval at block 656. The process returns to block 602. If the RRI is a tachyarrhythmia interval and the signal segment is not classified as a noise segment ("no" branch of block 654), the RRI is counted as a tachyarrhythmia interval at block 658.

When at least one tachyarrhythmia detection criterion is met at block 614, e.g., the NID is reached by the VT or VF interval counter, the VT or VF is detected at block 618 and a programmed therapy is delivered at block 618. In this way, a tachyarrhythmia detection is effectively withheld or not made in response to an RRI that is tachyarrhythmia interval but is associated with an R-wave sensed event signal corresponding to a cardiac electrical signal segment classified as a noise segment.

Figure 13:
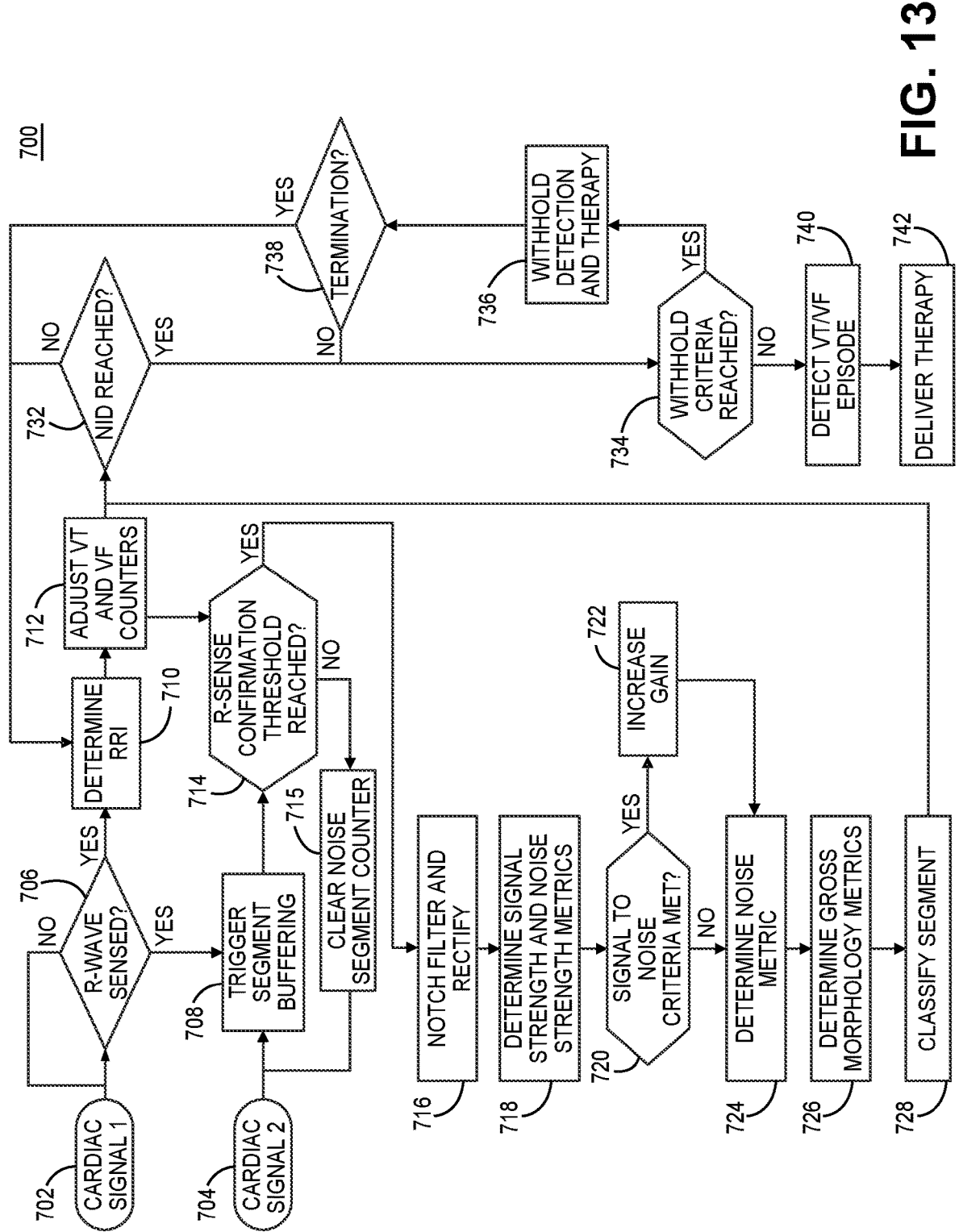
FIG. 13 is a flow chart of a method performed by a medical device for detecting non-cardiac noise and rejecting a ventricular tachyarrhythmia detection in response to detecting noise according to another example.

FIG. 13 is a flow chart 700 of a method performed by ICD 14 for detecting non-cardiac noise and rejecting a ventricular tachyarrhythmia detection in response to detecting noise according to another example. At blocks 702 and 704, two different cardiac electrical signals may be received by sensing circuit 86. In some examples, two different sensing electrode vectors may be selected by sensing circuit 86 for receiving a first cardiac electrical signal by a first sensing channel 83 and a second cardiac electrical signal by a second sensing channel 85, respectively. The two sensing electrode vectors may be selected by switching circuitry included in sensing circuit 86 under the control of control circuit 80. In some examples, the two sensing electrode vectors are programmed by a user and retrieved from memory 82 by control circuit 80 and passed to sensing circuit 86 as vector selection control signals.

In some examples, the first sensing electrode vector selected for sensing the first cardiac electrical signal at block 702 may be a relatively short bipole, e.g., between electrodes 28 and 30 or between electrodes 28 and 24 of lead 16 or other electrode combinations as described above. The relatively short bipole may include electrodes that are in relative close proximity to each other and to the ventricular heart chambers to provide sensing of a relatively "near-field" ventricular signal for sensing R-waves compared to a second sensing vector selected at block 704. The first sensing electrode vector may be a vertical sensing vector (with respect to an upright or standing position of the patient) or approximately aligned with the cardiac axis for maximizing the amplitude of R-waves in the first cardiac electrical signal for reliable R-wave sensing. The first sensing electrode vector, however, is not limited to any particular interelectrode spacing or orientation and may be selected as any available electrode pair.

The second sensing electrode vector used to receive a second cardiac electrical signal at block 704 may be a relatively longer bipole having an inter-electrode distance that is greater than the first sensing electrode vector. For example, the second sensing electrode vector may be selected as the vector between one of the pace sense electrodes 28 or 30 and ICD housing 15, one of defibrillation electrodes 24 or 26 and housing 15 or other combinations of one electrode along the distal portion of the lead 16 and the housing 15. This second sensing electrode vector may be orthogonal or almost orthogonal to the first sensing electrode vector in some examples, but the first and second sensing vectors are not required to be orthogonal vectors. The second sensing electrode vector may receive a relatively more global or far-field cardiac electrical signal compared to the first sensing electrode vector. The second cardiac electrical signal received by the second sensing channel 85 at block 304 may be analyzed by control circuit 80 for detecting noise corruption of both of the first and second cardiac electrical signals. In other examples, the first and second cardiac electrical signals sensed at blocks 702 and 704 may be received from the same sensing electrode vector, such that a single cardiac electrical signal is received by the sensing circuit 86, but the raw, received signal may be processed by two different sensing channels 83 and 85 of sensing circuit 86 having different filtering and/or other signal processing features to sense two different cardiac electrical signals, one used by the first sensing channel 83 for detecting R-waves and one sensed by the second sensing channel 85 for detecting noise and performing tachyarrhythmia morphology analysis. In still other examples, a single cardiac signal is used for sensing R-waves and buffered for detecting noise corruption of the cardiac signal.

Sensing circuit 86 may produce an R-wave sensed event signal at block 706 in response to the first sensing channel 83 detecting an R-wave sensing threshold crossing by the first cardiac electrical signal. The R-wave sensed event signal may be passed to control circuit 80. In response to the R-wave sensed event signal, down-going "yes" branch of block 706, control circuit 80 is triggered at block 708 to store a segment of the second cardiac electrical signal received from the second sensing channel 85 over a predetermined time interval. Segments of the second cardiac electrical signal may be stored in a circulating buffer of memory 82 configured to store multiple sequential segments, where storage of each segment is triggered by an R-wave sensed event signal produced by the first sensing channel 83. A digitized segment of the second cardiac electrical signal may be 100 to 500 ms long, for example, including sample points before and after the time of the R-wave sensed event signal. The segment of the second cardiac electrical signal may or may not be centered in time on the R-wave sensed event signal received from sensing circuit 86. For instance, the segment may extend 100 ms after the R-wave sensed event signal and be 200 to 500 ms in duration such that the segment extends from about 100 to 400 ms before the R-wave sensed event signal to 100 ms after. In other examples, the segment may be centered on the R-wave sensed event signal or extend a greater number of sample points after the R-wave sensed event signal than before. In one example, the buffered segment of the cardiac electrical signal is at least 50 sample points obtained at a sampling rate of 256 Hz, or about 200 ms. In another example, the buffered segment is at least 92 sample points, or approximately 360 ms, sampled at 256 Hz and is available for analysis for detecting noise present in the cardiac electrical signal segment.

Memory 82 may be configured to store a predetermined number of second cardiac electrical segments, e.g., at least 1 and in some cases two or more cardiac electrical signal segments, in circulating buffers such that the oldest segment is overwritten by the newest segment. However, previously stored segments may never be analyzed for noise detection and be overwritten if an R-sense confirmation threshold is not reached at block 714 as described below. In some examples, at least one segment of the second cardiac electrical signal may be stored and if not needed for detecting noise (before noise analysis criteria are met), the segment is overwritten by the next segment corresponding to the next R-wave sensed event signal.

In addition to buffering a segment of the second cardiac electrical signal, control circuit 80 responds to the R-wave sensed event signal produced at block 706 by determining an RRI at block 710 ending with the current R-wave sensed event signal and beginning with the most recent preceding R-wave sensed event signal. The timing circuit 90 of control circuit 80 may pass the RRI timing information to the tachyarrhythmia detection circuit 92 which adjusts tachyarrhythmia interval counters at block 312. If the RRI is longer than a tachycardia detection interval (TDI), the tachyarrhythmia interval counters remain unchanged. If the RRI is shorter than the TDI but longer than a fibrillation detection interval (FDI), e.g., if the RRI is in a tachycardia detection interval zone, a VT interval counter is increased at block 712. If the RRI is shorter than or equal to the FDI, a VF interval counter is increased at block 712. In some examples, a combined VT/VF interval counter is increased if the RRI is less than the TDI.

After updating the tachyarrhythmia interval counters at block 712, tachyarrhythmia detector 92 compares the counter values to an R-sense confirmation threshold at block 714 to determine if noise analysis criteria are met and to VT and VF detection thresholds at block 732 to determine if a respective NID is met. If a VT or VF detection interval counter has reached an R-sense confirmation threshold, "yes" branch of block 714, the second cardiac electrical signal, e.g., from sensing channel 85 is analyzed to detect noise corruption of the signal segment that may be causing false R-wave sensed event signals to be produced by the first sensing channel 83, resulting in VT and/or VF counters being increased at block 712. The R-sense confirmation threshold may be a VT or VF interval count value that is greater than one or another higher threshold count value. Different R-sense confirmation thresholds may be applied to the VT interval counter and the VF interval counter. For example, the R-sense confirmation threshold may be a count of two on the VT interval counter and a count of three on the VF interval counter. In other examples, the R-sense confirmation threshold is a higher number, for example five or higher, but may be less than the number of VT or VF intervals required to detect VT or VF. In addition or alternatively to applying an R-sense confirmation threshold to the individual VT and VF counters, an R-sense confirmation threshold may be applied to a combined VT/VF interval counter. It is recognized that in some examples, VT detection may not be enabled and VF detection may be enabled. In this case, only a VF interval counter is updated at block 712 in response to RRI determinations and the R-sense confirmation threshold may be applied to the VF interval counter at block 714.

If the R-sense confirmation threshold is not reached by any of the tachyarrhythmia interval counters at block 714, the control circuit 80 waits for the next R-wave sensed event signal at block 708 to buffer the next segment of the second cardiac electrical signal. If the R-sense confirmation threshold is reached at block 714, e.g., when the VF interval counter is greater than 2, the control circuit 80 begins analysis of the second cardiac electrical signal segments for detecting noise segments.

At block 716, control circuit 80 may retrieve one or more notch filtered signal segments stored in memory 82. In some examples, the stored second cardiac electrical signal segments are notch filtered and rectified by control circuit 80 at block 716, e.g., by a software, firmware or hardware implemented notch filter and rectifier, after the R-sense confirmation threshold is reached. In other examples, the notch-filtered, rectified signal is received from the second sensing channel 85 as shown in FIG. 4 and buffered in memory 82 for retrieval by control circuit 80. As described above, the notch-filter may be implemented to attenuate 50 Hz and 60 Hz line frequency noise.

At block 718, control circuit 80 determines a signal strength metric and a noise strength metric for use in identifying noise segments after the R-sense confirmation threshold is reached. The signal strength metric and the noise metric may be determined from each notch-filtered second cardiac electrical signal segment buffered in response to an R-wave sensed event signal in some examples. In one example, control circuit 80 may determine the signal strength metric as the maximum amplitude of the notch-filtered rectified signal segment. Additionally, control circuit 80 may determine the noise strength metric by determining a rectified, differential signal (or high pass filtered signal) and determining its maximum amplitude as the noise strength metric at block 718. The maximum amplitude of each buffered signal segment over a predetermined time interval, e.g., 1.2 seconds, and the maximum amplitude of the current differential signal segment may be used by control circuit 80 to determine if signal to noise criteria are met at block 720 in some examples.

As described above in conjunction with FIG. 5, the greatest maximum amplitude of all segments during the time interval may be compared to a signal strength threshold, e.g., one-third of the dynamic range of the ADC or other selected threshold, and the differential signal maximum amplitude of the current cardiac electrical signal segment may be compared to a noise strength threshold, e.g., 13 ADC units or other predetermined value or selected threshold. When the greatest maximum amplitude is greater than the signal strength threshold and the maximum differential signal amplitude of the current signal segment is less than the noise strength threshold, the signal to noise criteria may be met at block 720. In other examples, a ratio of the greatest maximum amplitude over a predetermined time interval and the differential signal maximum amplitude of the current signal segment may be compared to a signal to noise threshold ratio to determine if the signal to noise criteria are met at block 720.

When the signal to noise criteria are met, the gain of the differential signal is increased at block 722 by control circuit 80. Otherwise, the gain remains unchanged. Control circuit 80 determines a noise metric, e.g., the noise pulse count, at block 724 using either the differential signal with unchanged gain or the differential signal with increased gain. The methods for determining the noise metric by determining a noise pulse count as described above in conjunction with FIGS. 7-8 may be performed at block 724. In other examples, a different noise metric such as any of the examples given above may be determined from the current signal segment.

In addition to determining the noise metric, control circuit 80 may optionally determine the gross morphology metric(s) at block 726 for detecting a tachyarrhythmia waveform morphology at block 726 as generally described in conjunction with FIGS. 9 and 10 above. Based on the noise pulse count (or other noise metric), and the tachyarrhythmia waveform morphology metric(s) when determined, the current second cardiac electrical signal segment may be classified at block 728. As described above, when the noise metric meets a noise detection threshold and the gross morphology metric(s) do not meet a tachyarrhythmia morphology criteria, the segment may be classified as a noise segment by control circuit 80 at block 728. When the noise metric is less than or equal to a noise detection threshold or at least one gross morphology metric meets a tachyarrhythmia morphology criterion, the segment may be classified as a non-noise segment by control circuit 80 at block 728.

After classifying the current segment, control circuit 80 may determine if the NID has been reached by the VT, VF or combined VT/VF interval counters at block 732. When a threshold number of intervals to detect (NID) is not reached by the VT interval counter, VF interval counter, or combined VT/VF interval counter, control circuit 80 returns to block 710 to continue determining RRIs and analyzing second cardiac electrical signal segments as long as the R-sense confirmation threshold is satisfied (block 714). If the R-sense confirmation threshold is no longer met at block 714, the noise segment counter or buffer may be cleared at block 715.

When the NID is reached at block 732, based on the values of the VT and/or VF interval counters, control circuit 80 determines whether a withhold detection threshold number of noise segments has been reached at block 734. The VT or VF detection based on the NID being reached is withheld at block 734 in response to a withhold threshold number of the most recent cardiac electrical signal segments being classified as noise segments. In one example, if at least two out of the most recent eight cardiac electrical signal segments are classified as noise segments, the withhold detection threshold is met at block 734. The VT or VF detection (and any associated VT or VF therapy) is withheld by control circuit 80 at block 736. The ventricular tachyarrhythmia is not detected by control circuit 80 when a threshold number of the most recent signal segments are classified as noise segments even when a tachyarrhythmia detection criterion, e.g., the NID, is reached. As long as the NID continues to be met, control circuit 80 may continue to classify and count noise segments as new R-waves are sensed to determine if the withhold threshold is still being met at block 734.

In some examples, control circuit 80 may determine if termination criteria are met at block 738 when detection has been withheld. Termination of the fast rhythm may be detected based on a predetermined number of RRIs that are greater than a tachyarrhythmia detection interval or when a mean, median or other metric of RRIs determined over predetermined time interval is greater than a tachyarrhythmia detection interval. For example, when a threshold number of RRIs longer than the VT detection interval (e.g., when VT detection is enabled) or longer than the VF detection interval (e.g., when VT detection is not enabled) are detected subsequent to the NID being met, tachyarrhythmia termination may be detected at block 738. In one example, termination is detected at block 738 when at least eight consecutive long RRIs, e.g., greater than the VT detection interval, are detected. In another example, control circuit 80 may detect termination at block 738 when a predetermined time interval elapses and a median RRI is greater than the VT detection interval. For instance, when the median RRI of the most recent 12 RRIs is always greater than the VT detection interval for at least 20 seconds, or other predetermined time period, control circuit 80 may detect termination at block 738. Control circuit 80 may reset the VT and VF interval counters and the count of noise segments and return to block 710 in response to detecting termination.

When the NID is met at block 732 and the withhold threshold is not reached at block 734, e.g., less than a threshold number of noise segments being classified, a VT or VF episode is detected at block 740. Therapy delivery circuit 84 may deliver a VT or VF therapy at block 742 in response to the VT/VF detection. It is to be understood that other criteria besides the NID criterion may be applied before detecting the VT or VF at block 740. For example, various P-wave oversensing rejection criteria, T-wave oversensing rejection criteria, supraventricular tachycardia (SVT) rejection criteria, etc. may be required to be unmet and/or tachyarrhythmia onset criteria, tachyarrhythmia morphology criteria, etc. may be required to be met before detecting VT/VF at block 740 and delivering therapy at block 742.

It is contemplated that in other examples, the VT/VF detection may be made in response to detection criteria being satisfied, e.g., the NID being reached at block 732, but the VT/VF therapy may be withheld at block 736 when the withhold threshold is reached or exceeded by the number of noise segments detected. Therapy delivery circuit 84 may withhold a VT or VF therapy until the withhold threshold is no longer reached and the tachyarrhythmia is still being detected. Therapy delivery circuit 84 may deliver a withheld therapy when the withhold threshold is no longer met and termination of the detected VT or VF has not been detected at block 738. If the detected VT or VF is determined to be terminated at block 738 while the therapy is being withheld, the noise segment count and VT/VF interval counters may be cleared and the process may return to block 710 without ever delivering a therapy.

It should be understood that, depending on the example, certain acts or events of any of the methods described herein can be performed in a different sequence, may be added, merged, or left out altogether (e.g., not all described acts or events are necessary for the practice of the method). Moreover, in certain examples, acts or events may be performed concurrently, e.g., through multi-threaded processing, interrupt processing, or multiple processors, rather than sequentially. In addition, while certain aspects of this disclosure are described as being performed by a single circuit or unit for purposes of clarity, it should be understood that the techniques of this disclosure may be performed by a combination of units or circuits associated with, for example, a medical device.

In one or more examples, the functions described may be implemented in hardware, software, firmware, or any combination thereof. If implemented in software, the functions may be stored as one or more instructions or code on a computer-readable medium and executed by a hardware-based processing unit. Computer-readable media may include computer-readable storage media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPLAs), or other equivalent integrated or discrete logic circuitry. Accordingly, the term "processor," as used herein may refer to any of the foregoing structure or any other structure suitable for implementation of the techniques described herein. Also, the techniques could be fully implemented in one or more circuits or logic elements.

Thus, a medical device has been presented in the foregoing description with reference to specific examples. It is to be understood that various aspects disclosed herein may be combined in different combinations than the specific combinations presented in the accompanying drawings. It is appreciated that various modifications to the referenced examples may be made without departing from the scope of the disclosure and the following claims.

What is claimed is:

1. A medical device comprising:
a sensing circuit configured to:
sense at least one cardiac electrical signal; and
sense cardiac electrical event signals attendant to ventricular myocardial depolarizations from the at least one electrical signal;
a memory; and
a control circuit in communication with the memory and the sensing circuit and configured to:
buffer in the memory, in response to a first cardiac electrical event signal sensed by the sensing circuit, a first signal segment from the at least one cardiac electrical signal sensed by the sensing circuit;
determine a pulse detection threshold amplitude from the first signal segment;
determine that the pulse detection threshold amplitude is less than a suspected noise threshold; and
in response to the pulse detection threshold amplitude being less than the suspected noise threshold, determine that the first signal segment is a non-noise segment.

2. The medical device of claim 1 wherein the control circuit is further configured to:
determine a maximum peak amplitude of the first signal segment; and
determine the pulse detection threshold amplitude based on the maximum peak amplitude.

3. The medical device of claim 1 wherein the control circuit is further configured to:
obtain, in response to a second cardiac electrical event signal sensed by the sensing circuit, a second signal segment from the at least one cardiac electrical signal sensed by the sensing circuit;
determine a second pulse detection threshold amplitude from the second signal segment;
determine that the second pulse detection threshold amplitude is not less than the suspected noise threshold; and
in response to the second pulse detection threshold amplitude not being less than the suspected noise threshold, determine a noise metric from the second signal segment.

4. The medical device of claim 3 wherein the control circuit is further configured to:
compare the noise metric to a noise threshold; and
classify the second signal segment as one of a noise segment or a non-noise segment based on the comparison.

5. The medical device of claim 3 wherein the control circuit is further configured to determine the noise metric by:
identifying signal pulses from the second signal segment; and
determining a count of the identified signal pulses.

6. The medical device of claim 5 wherein the control circuit is further configured to identify signal pulses from the second signal segment by at least identifying signal pulses of the second signal segment having a peak amplitude that is greater than the second pulse detection threshold amplitude.

7. The device of claim 1 wherein the control circuit is further configured to:
classify each of a plurality of signal segments comprising the first signal segment as one of a noise segment or a non-noise segment;
determine that less than a threshold number of the plurality of signal segments are classified as noise segments; and
detect a tachyarrhythmia based on the at least one cardiac electrical signal and less than the threshold number of the plurality of signal segments being classified as noise segments.

8. The medical device of claim 7 further comprising a therapy delivery circuit configured to generate a tachyarrhythmia therapy in response to the control circuit detecting the tachyarrhythmia.

9. The device of claim 1 wherein the control circuit is further configured to:
classify each of a plurality of signal segments comprising the first signal segment as one of a noise segment or a non-noise segment;
determine that at least a threshold number of the plurality of signal segments are classified as noise segments;
detect a required number of tachyarrhythmia intervals to detect a tachyarrhythmia based on the cardiac electrical event signals sensed by the sensing circuit; and
in response to determining that at least the threshold number of the plurality of signal segments are classified as noise segments, withhold detecting the tachyarrhythmia when the required number of tachyarrhythmia intervals are detected.

10. The medical device of claim 1 further comprising a therapy delivery circuit configured to deliver an electrical stimulation therapy,
wherein the control circuit is further configured to control the delivery of the electrical stimulation therapy by the therapy delivery circuit based on at least the first cardiac electrical event signal in response to the first signal segment being a non-noise segment.

11. A method comprising:
sensing at least one cardiac electrical signal by a sensing circuit;
sensing cardiac electrical event signals attendant to ventricular myocardial depolarizations from the at least one electrical signal;
buffering in a memory, in response to a first cardiac electrical event signal sensed by the sensing circuit, a first signal segment from the at least one cardiac electrical signal;
determining a pulse detection threshold amplitude from the first signal segment;
determining that the pulse detection threshold amplitude is less than a suspected noise threshold; and
in response to the pulse detection threshold amplitude being less than the suspected noise threshold, determining that the first signal segment is a non-noise segment.

12. The method of claim 11 further comprising:
determining a maximum peak amplitude of the first signal segment; and
determining the pulse detection threshold amplitude based on the maximum peak amplitude.

13. The method of claim 11 further comprising:
obtaining, in response to a second cardiac electrical event signal sensed by the sensing circuit, a second signal segment from the at least one cardiac electrical signal sensed by the sensing circuit;
determining a second pulse detection threshold amplitude from the second signal segment;
determining that the second pulse detection threshold amplitude is not less than the suspected noise threshold; and in response to the second pulse detection threshold amplitude not being less than the suspected noise threshold, determining a noise metric from the second signal segment.

14. The method of claim 13 further comprising:
comparing the noise metric to a noise threshold; and
classifying the second signal segment as one of a noise segment or a non-noise segment based on the comparison.

15. The method of claim 13 wherein determining the noise metric comprises:
identifying signal pulses from the second signal segment; and
determining a count of the identified signal pulses.

16. The method of claim 15 wherein identifying signal pulses from the second signal segment comprises at least identifying signal pulses of the second signal segment having a peak amplitude that is greater than the second pulse detection threshold amplitude.

17. The method of claim 11 further comprising:
classifying each of a plurality of signal segments comprising the first signal segment as one of a noise segment or a non-noise segment;
determining that less than a threshold number of the plurality of signal segments are classified as noise segments; and
detecting a tachyarrhythmia based on the at least one cardiac electrical signal and less than the threshold number of the plurality of signal segments being classified as noise segments.

18. The method of claim 17 further comprising generating a tachyarrhythmia therapy in response to detecting the tachyarrhythmia.

19. The method of claim 11 further comprising:
classifying each of a plurality of signal segments comprising the first signal segment as one of a noise segment or a non-noise segment;
determining that at least a threshold number of the plurality of signal segments are classified as noise segments; and
detecting a required number of tachyarrhythmia intervals to detect a tachyarrhythmia based on the sensed cardiac electrical event signals; and
in response to determining that at least the threshold number of the plurality of signal segments are classified as noise segments, withholding detecting the tachyarrhythmia when the required number of tachyarrhythmia intervals are detected.

20. The method of claim 11 further comprising controlling delivery of an electrical stimulation therapy based on at least the first cardiac electrical event signal in response to the first signal segment being a non-noise segment.

21. A non-transitory computer-readable medium storing a set of instructions which, when executed by a control circuit of a medical device, cause the medical device to:
sense at least one cardiac electrical signal;
sense cardiac electrical event signals attendant to ventricular myocardial depolarizations from the at least one electrical signal;
buffer in a memory, in response to a cardiac electrical event signal sensed by the sensing circuit, a signal segment from the at least one cardiac electrical signal;
determining a pulse detection threshold amplitude from the signal segment;
determining that the pulse detection threshold amplitude is less than a suspected noise threshold; and
in response to the pulse detection threshold amplitude being less than the suspected noise threshold, determining that the signal segment is a non-noise segment.

* * * * *